(12) United States Patent
Nishihara et al.

(10) Patent No.: US 7,858,290 B2
(45) Date of Patent: *Dec. 28, 2010

(54) INFORMATION RECORDING MEDIUM AND METHOD FOR MANUFACTURING THE SAME

(75) Inventors: Takashi Nishihara, Hirakata (JP); Yukako Doi, Takatsuki (JP); Rie Kojima, Kadoma (JP); Noboru Yamada, Hirakata (JP)

(73) Assignee: Panasonic Corporation, Osaka (JP)

( * ) Notice: Subject to any disclaimer, the term of this patent is extended or adjusted under 35 U.S.C. 154(b) by 1289 days.

This patent is subject to a terminal disclaimer.

(21) Appl. No.: 10/953,687

(22) Filed: Sep. 29, 2004

(65) Prior Publication Data

US 2005/0074694 A1    Apr. 7, 2005

(30) Foreign Application Priority Data

Oct. 2, 2003    (JP)    ............... 2003-344944

(51) Int. Cl.
*G11B 7/24*    (2006.01)
*C23C 14/00*    (2006.01)
*C23C 14/32*    (2006.01)

(52) U.S. Cl. ............... 430/270.13; 430/945; 369/275.2; 369/275.5; 428/64.6

(58) Field of Classification Search ........................ None
See application file for complete search history.

(56) References Cited

U.S. PATENT DOCUMENTS

| | | | |
|---|---|---|---|
| 6,096,399 A * | 8/2000 | Yoshinari et al. | ........... 428/64.1 |
| 6,406,771 B1 * | 6/2002 | Nakakuki et al. | ........... 428/64.1 |
| 6,456,584 B1 | 9/2002 | Nagata et al. | |
| 6,503,690 B1 * | 1/2003 | Uno et al. | ............ 430/270.13 |
| 6,670,014 B2 | 12/2003 | Nishihara et al. | |
| 7,063,876 B2 * | 6/2006 | Nishihara et al. | ........... 428/64.1 |
| 2001/0041304 A1 | 11/2001 | Uno et al. | |
| 2002/0054983 A1 | 5/2002 | Nishihara et al. | |
| 2003/0124387 A1 * | 7/2003 | Hirotsune et al. | ..... 428/694 ML |
| 2003/0138669 A1 * | 7/2003 | Kojima et al. | ........... 428/694 ST |
| 2003/0180473 A1 | 9/2003 | Nishihara et al. | |

FOREIGN PATENT DOCUMENTS

| | | | |
|---|---|---|---|
| CN | 1347082 | | 5/2002 |
| CN | 1445767 | | 10/2003 |
| EP | 1005036 | * | 5/2000 |
| EP | 1 324 326 | | 7/2003 |
| EP | 1 349 160 | | 10/2003 |
| EP | 1 501 090 | | 1/2005 |
| EP | 1 575 043 | | 9/2005 |
| JP | 05159368 | * | 6/1993 |
| JP | 10-275360 | | 10/1998 |
| JP | 2000-36130 | | 2/2000 |
| JP | 2000-339750 | | 12/2000 |
| JP | 2001-67722 | | 3/2001 |
| JP | 2001-067722 | * | 3/2001 |
| JP | 2002-144736 | | 5/2002 |
| JP | 2003-242683 | * | 8/2003 |

OTHER PUBLICATIONS

Translation of JP-2001-067722(Mar. 2001).*
Translation of JP-2003-242683(Aug. 2003).*

* cited by examiner

*Primary Examiner*—Cynthia H Kelly
*Assistant Examiner*—Anna L Verderame
(74) *Attorney, Agent, or Firm*—Hamre, Schumann, Mueller & Larson, P.C.

(57) ABSTRACT

An information recording medium includes a substrate and an information layer formed on the substrate. The information layer includes a recording layer whose phase can be changed between a crystalline phase and an amorphous phase by irradiation with a laser beam or application of electric energy; a Cr-containing layer including at least Cr and O, arranged in contact with a first surface of the recording layer; and a Ga-containing layer including at least Ga and O, arranged in contact with a second surface of the recording layer.

24 Claims, 11 Drawing Sheets

INFORMATION RECORDING MEDIUM AND METHOD FOR MANUFACTURING THE SAME

BACKGROUND OF THE INVENTION

1. Field of the Invention

The present invention relates to an information recording medium that is capable of recording, erasing, rewriting and reproducing information optically or electrically, as well as to a method for manufacturing the same.

2. Related Background Art

As conventional information recording media, phase-changing information recording media are known that record, erase and rewrite information using the phenomenon that a phase change between a crystalline phase and an amorphous phase occurs in a recording layer (phase-changing material layer) that is made of a phase-changing material. Among such phase-changing information recording media, there are optical phase-changing information recording media, with which information can be recorded, erased, rewritten and reproduced using a laser beam. In these optical phase-changing information recording media heat generated by irradiation of a laser beam causes a phase change between the crystalline phase and the amorphous phase in the phase-changing material of the recording layer, and differences in the reflectance of the crystalline phase and the amorphous phase are detected and read out as information. In rewritable optical phase-changing information recording media, which allow the erasing and rewriting of information, the initial state of the recording layer is ordinarily the crystalline phase, and to record information, the recording layer is melted through irradiation of a laser beam of high power (recording power) and rapidly cooled down, turning the portions on which the laser beam was irradiated (laser beam irradiation portions) into the amorphous phase. On the other hand, to erase information, the recording layer is heated by irradiating a laser beam of a power that is lower than during recording (erasing power) and slowly cooled, thus turning the laser beam irradiation portions into the crystalline phase. Consequently, in rewritable optical phase-changing information recording media, it is possible to record new information while erasing recorded information, that is, to rewrite information, by irradiating onto the recording layer a laser beam whose power is modulated between a high power level and a low power level. Moreover, in write-once optical phase-change information recording media in which information can be recorded once, but cannot be erased or rewritten, the recording layer is generally in the amorphous phase in its initial state. To record information on such a recording medium, the recording layer is heated by irradiating a laser beam with high power (recording power), and then slowly cooled, thus turning the laser beam irradiation portions into the crystalline phase.

There are also electrical phase-change information recording media, in which information is recorded by phase-changing the phase-changing material of the recording layer through joule heat that is generated by applying electric energy (for example an electric current) instead of irradiating a laser beam. In such electrical phase-change information recording media, the phase-changing material of the recording layer undergoes a phase change between a crystalline phase (low resistance) and an amorphous phase (high resistance) due to joule heat that is generated by applying a current, for example, and information is read out by detecting the difference in electric resistance between the crystalline phase and the amorphous phase.

An example of optical phase-change information recording media is the 4.7 GB DVD-RAM (digital versatile disk—random access memory) proposed by the inventors (see for example JP H10-275360A). Like the information recording medium 12 shown in FIG. 12, this 4.7 GB DVD-RAM includes, from the side from which a laser beam 11 is irradiated, a substrate 1, and an information layer 100 having a seven-layer structure including a first dielectric layer 2, a first interface layer 3, a recording layer 4, a second interface layer 5, a second dielectric layer 6, a light-absorbing correction layer 7, and a reflective layer 8, layered in this order on top of the substrate 1.

The first dielectric layer 2 and the second dielectric layer 6 have the optical function of increasing the optical absorption efficiency by adjusting the optical distance and increasing the signal intensity by increasing the change of the reflectance between when the recording layer 4 is in the crystalline phase and when it is in the amorphous phase, and furthermore have the thermal function of thermally insulating the recording layer 4, which becomes hot during recording, from the substrate 1 and the dummy substrate 10, which are easily damaged by heat. Conventionally, a mixture of 80 mol % ZnS and 20 mol % $SiO_2$ (referred to below as $(ZnS)_{80}(SiO_2)_{20}$ (mol %) or $(ZnS)_{80}(SiO_2)_{20}$; the same notation also is used for other mixtures) is used for the dielectric layers. This mixture is a superior dielectric material, which is transparent, has a high refractive index, a low thermal conductivity, and a good thermal insulation, and has favorable mechanical characteristics and moisture resistance. It should be noted that the film thickness of the first dielectric layer 2 and the second dielectric layer 6 can be determined strictly by calculation with the matrix method, such that the following conditions are satisfied: the change of the reflected light amount between the crystalline phase and the amorphous phase of the recording layer 4 is large, and the optical absorption at the recording layer 4 is large. By using for the recording layer 4 a high-speed crystallizing material including Ge—Sn—Sb—Te, in which some of the Ge in the pseudo-binary system phase-changing material GeTe—$Sb_2Te_3$ obtained by mixing the compounds GeTe and $Sb_2Te_3$, is substituted with Sn, it is possible to realize not only initial recording/rewriting properties, but also excellent archival characteristics (indicating whether a recorded signal can be reproduced after storage for a long time), and archival overwrite characteristics (indicating whether a recorded signal can be erased or rewritten after storage for a long time).

The first interface layer 3 and the second interface layer 5 have the function of preventing substance migration that otherwise may occur between the first dielectric layer 2 and the recording layer 4 or between the second dielectric layer 6 and the recording layer 4. Here, "substance migration" refers to the phenomenon that if $(ZnS)_{80}(SiO_2)_{20}$ (mol %) is used for the first dielectric layer 2 and the second dielectric layer 6, sulfur in the $(ZnS)_{80}(SiO_2)_{20}$ (mol %) diffuses into the recording layer when repeatedly writing/rewriting the recording layer 4 through irradiation of the laser beam 11. When sulfur diffuses into the recording layer, the repeated rewriting properties deteriorate. In order to prevent this deterioration of the repeated rewriting properties, it is advantageous to use a nitride including Ge for the first interface layer 3 and the second interface layer 5.

With the above-described technology, excellent repeated rewriting properties and high reliability were achieved, and a 4.7 GB DVD-RAM was proposed and brought to market.

Various technologies have been studied to increase the capacity of information recording media even further. For example, for optical phase-changing information recording media, a technology has been studied in which high-density recording is performed by reducing the spot diameter of the laser beam by using a bluish-purple laser having a wavelength that is shorter than that of conventional red lasers, or by making the substrate on the side from which the laser beam is irradiated thin and using an objective lens having a large numerical aperture (NA). When recording with smaller spot diameters, the time for which the laser beam is irradiated onto the recording layer becomes relatively short. Therefore, in order to enable crystallization with shorter times, it is necessary to make the recording layer from a more readily crystallizing material, or to provide a layer with a high crystallization enhancing effect adjacent to the recording layer.

Furthermore, technologies have been studied by which the recording capacity is doubled by using optical phase-changing information recording media having two information layers (in the following also referred to as "double-layer optical phase-changing information recording media") and recording and reproducing information on two information layers with a laser beam that is irradiated from one side (see for example JP 2000-36130A and JP 2002-144736A). In double-layer optical phase-changing information recording media, in order to record/reproduce the information layer that is located further away from the side from which the laser beam is incident (referred to as "second information layer" in the following), a laser beam is used that passes through the information layer located closer to the side from which the laser beam is incident (referred to as "first information layer" in the following), so that in the first information layer, the recording layer is made thin and its transmittance is increased. However, when the recording layer becomes thin, the number of crystal nuclei that are formed when the recording layer is crystallized is reduced, and the distance over which atoms can move is shortened. Therefore, the thinner the recording layer is, the more difficult it becomes to form the crystalline phase becomes (i.e. the crystallization speed decreases). Consequently, in a first information layer having a thin recording layer, it is necessary to make the recording layer from a material with better crystallization capability or to provide a layer with a high crystallization enhancing effect adjacent to the recording layer.

Furthermore, when the time it takes to record information on the information recording medium is shortened and the information transfer rate is increased, the time for crystallization also becomes short. Therefore, also in order to realize phase-changing information recording media for high transfer rates, it is again necessary to make the recording layer from a material with better crystallization capability or to provide a layer with a high crystallization enhancing effect adjacent to the recording layer.

Conventionally, in order to address this problem, and realize a medium with high capacity and suitable for high transfer rates, a material with high crystallization capability is used for the recording layer, and interface layers made of a nitride including Ge, as in the 4.7 GB DVD-RAM, are arranged on both sides of the recording layer.

However, when using a material in which the crystallization capability is increased in order to improve the crystallization speed of the optical phase-changing information recording medium, then the amorphous phase becomes difficult to form in particular in rewritable optical phase-changing information recording media. Therefore, it becomes necessary to heat the recording layer to a higher temperature, widen the melting region of the recording layer, and quickly cool the recording layer. Thus, a higher energy (laser power) becomes necessary to record information, and there is the problem that the recording sensitivity decreases. Moreover, when interface layers made of a nitride including Ge are used as in the conventional case, then there is the problem that the interface layers may be damaged by the heat generated in the recording layer by applying a large energy, considerably deteriorating the repeated rewriting properties.

Furthermore, since the thermal conductivity of nitrides including Ge is high, heat tends to diffuse in particular when the interface layer is thick. Also due to this reason, there is the problem that the recording sensitivity is decreased.

Moreover, when the interface layers are made of a nitride including Ge, then the extinction coefficient of the interface layers becomes large, so that light is absorbed more easily by the interface layers. When more light is absorbed by the interface layers, then there is the problem that the difference between the reflectance in the crystalline phase and the reflectance in the amorphous phase of the optical phase-changing information recording medium becomes small, and the signal intensity decreases. Moreover, more light is absorbed by the interface layers, so that there is the problem that the recording sensitivity decreases even further.

SUMMARY OF THE INVENTION

It is an object of the present invention to provide a phase-changing information recording medium with which the crystallization speed of the recording layer is increased while suppressing a decrease in recording sensitivity, repeated rewriting properties and signal intensity.

A first information recording medium according to the present invention comprises a substrate and an information layer provided on the substrate; the information layer comprising a recording layer whose phase can be changed between a crystalline phase and an amorphous phase by irradiation with a laser beam or application of electric energy; a Cr-containing layer comprising at least Cr and O, arranged in contact with a first surface of the recording layer; and a Ga-containing layer comprising at least Ga and O, arranged in contact with a second surface of the recording layer.

A second information recording medium according to the present invention comprises a substrate and an information layer provided on the substrate, the information layer comprising a recording layer whose phase can be changed between a crystalline phase and an amorphous phase by irradiation with a laser beam or application of electric energy; a first Ga-containing layer comprising at least Ga and O, arranged in contact with a first surface of the recording layer; and a second Ga-containing layer comprising at least Ga and O, arranged in contact with a second surface of the recording layer.

A third information recording medium according to the present invention comprises a substrate and an information layer provided on the substrate, the information layer comprising a recording layer whose phase can be changed between a crystalline phase and an amorphous phase by irradiation with a laser beam or application of electric energy; a first Cr-containing layer comprising at least Cr and O, arranged in contact with a first surface of the recording layer; a second Cr-containing layer comprising at least Cr and O, arranged in contact with a second surface of the recording layer; and a Ga-containing layer comprising at least Ga and O, arranged in contact with the second Cr-containing layer.

A fourth information recording medium according to the present invention comprises a substrate and an information layer provided on the substrate, the information layer comprising a recording layer whose phase can be changed between a crystalline phase and an amorphous phase by irradiation with a laser beam or application of electric energy; a Cr-containing layer comprising at least Cr and O, arranged on a side of a first surface of the recording layer; a Ga-containing layer comprising at least Ga and O, arranged on a side of a second surface of the recording layer; and a C-containing layer containing C as its principal component and arranged in contact with the recording layer between the recording layer and the Cr-containing layer and/or between recording layer and the Ga-containing layer.

A first information recording medium manufacturing method according to the present invention comprises:

(a) a step of forming a Cr-containing layer using a Cr-containing sputtering target comprising at least Cr and O;

(b) a step of forming a recording layer whose phase can be changed between a crystalline phase and an amorphous phase by irradiation with a laser beam or application of electric energy;

(c) a step of forming a Ga-containing layer using a Ga-containing sputtering target comprising at least Ga and O;

wherein the steps (a) to (c) are carried out in the order of step (a), step (b), step (c) or in the order of step (c), step (b), step (a).

A second information recording medium manufacturing method according to the present invention comprises:

(a) a step of forming a first Ga-containing layer using a first Ga-containing sputtering target comprising at least Ga and O;

(b) a step of forming a recording layer whose phase can be changed between a crystalline phase and an amorphous phase by irradiation with a laser beam or application of electric energy;

(c) a step of forming a second Ga-containing layer using a second Ga-containing sputtering target comprising at least Ga and O;

wherein the steps (a) to (c) are carried out in the order of step (a), step (b), step (c) or in the order of step (c), step (b), step (a).

A third information recording medium manufacturing method according to the present invention comprises:

(a) a step of forming a first Cr-containing layer using a first Cr-containing sputtering target comprising at least Cr and O;

(b) a step of forming a recording layer whose phase can be changed between a crystalline phase and an amorphous phase by irradiation with a laser beam or application of electric energy;

(c) a step of forming a second Cr-containing layer using a second Cr-containing sputtering target comprising at least Cr and O;

(d) a step of forming a Ga-containing layer using a second Ga-containing sputtering target comprising at least Ga and O;

wherein the steps (a) to (d) are carried out in the order of step (a), step (b), step (c), step (d) or in the order of step (d), step (c), step (b), step (a).

A fourth information recording medium manufacturing method according to the present invention comprises:

(a) a step of forming a Cr-containing layer using a Cr-containing sputtering target comprising at least Cr and O;

(b) a step of forming a recording layer whose phase can be changed between a crystalline phase and an amorphous phase by irradiation with a laser beam or application of electric energy;

(c) a step of forming a Ga-containing layer using a Ga-containing sputtering target comprising at least Ga and O;

wherein the steps (a) to (c) are carried out in the order of step (a), step (b), step (c) or in the order of step (c), step (b), step (a); and further comprising a step of forming a C-containing layer using a C-containing sputtering target comprising C as its principal component between step (a) and step (b) and/or between step (b) and step (c).

DETAILED DESCRIPTION OF THE INVENTION

Figure 1:
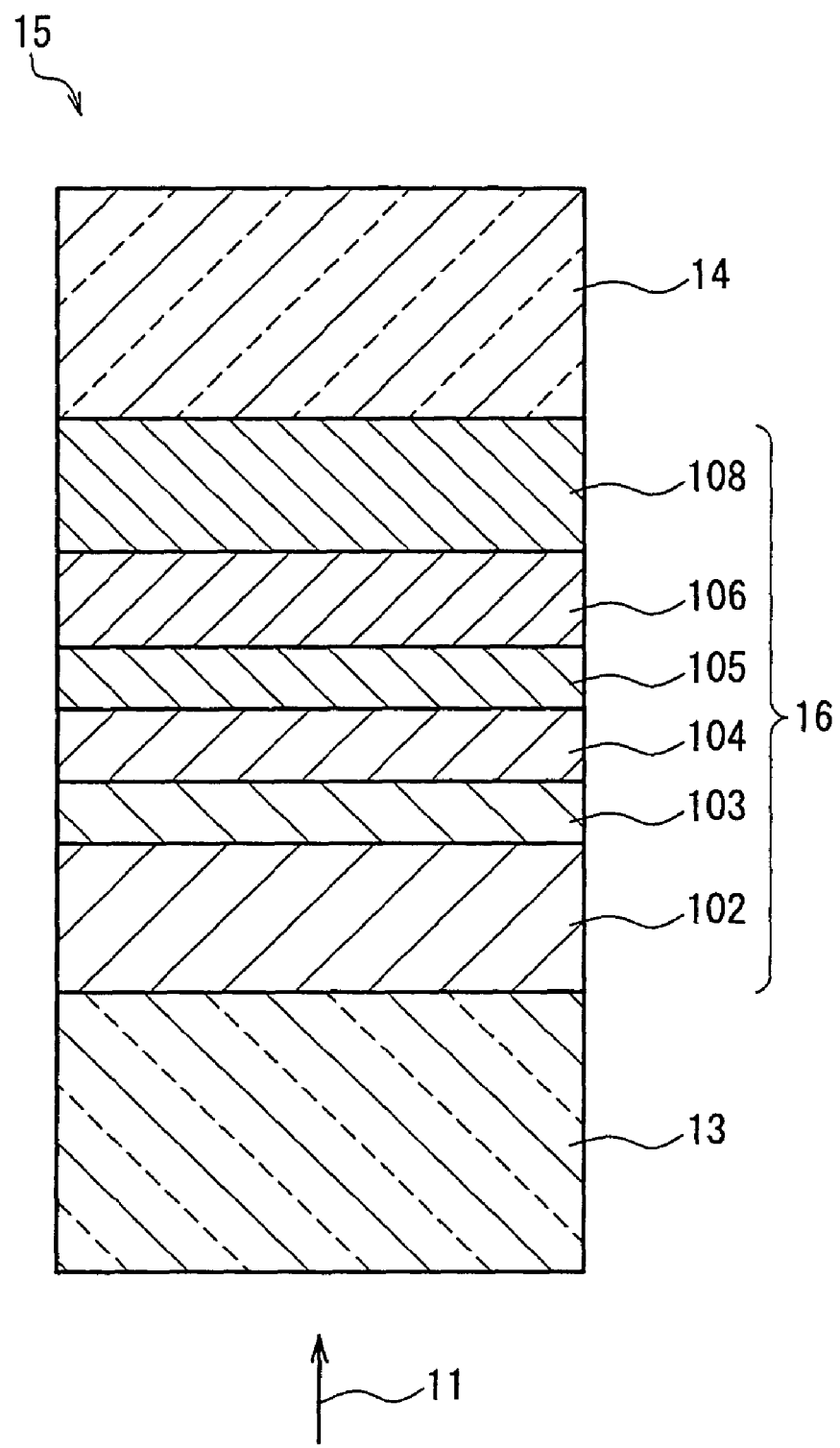
FIG. 1 is a partial cross-sectional view showing the configuration of an information recording medium according to Embodiment 1 of the present invention.

With the first to fourth information recording media, it is possible to provide phase-changing information recording media with a decrease in recording sensitivity, repeated rewriting properties and signal intensity suppressed and the crystallization speed of the recording layer increased.

If the first information recording medium is an optical information recording medium wherein the recording layer's phase can be changed between the crystalline phase and the amorphous phase by irradiation with a laser beam, then it is preferable that the Cr-containing layer, the recording layer and the Ga-containing layer are arranged in this order from a side from which the laser beam is incident. By arranging the Cr-containing layer closer to the side from which the laser beam is incident, it is possible to attain higher crystallization speed. By arranging the Ga-containing layer further away from the side from which the laser beam is incident, it is possible to suppress the thermal conduction from the recording layer and attain higher recording sensitivity. Accordingly, by arranging the Cr-containing layer and the Ga-containing layer in this way, it is possible to attain higher recording sensitivity, signal intensity and repeated rewriting properties. Moreover, in the case of an optical information recording medium, the information layer further may comprise at least one of a first dielectric layer arranged closer to the side from which the laser beam is incident than the Cr-containing layer, and a second dielectric layer arranged further away from the side from which the laser beam is incident than the Ga-containing layer. The information layer further may comprise a reflective layer arranged further away from the side from which the laser beam is incident than the Ga-containing layer. By providing at least one of the first and the second dielectric layer, or the reflective layer, the effect of increasing the optical absorption efficiency of the recording layer or the signal intensity or the like can be attained as well. It should be noted that in this specification, in order to distinguish dielectric layers or interface layers that are included in the same information layer, "first" and "second" is used in conjunction with the names of the dielectric layers and interface layers, where "first" means arranged on the side of the recording layer that is closer to the side from which the laser beam is irradiated and "second" means arranged on the side of the recording layer that is further away from the side from which the laser beam is irradiated.

The first information recording medium of the present invention also may be a multi-layer information recording medium comprising first to N-th information layers (where N is an integer of 2 or more), and wherein at least one of the first to N-th information layers is said information layer. In this case, it is preferable that at least one of the first to N-th information layers has the same film configuration as the information layer included in the above-described first information recording medium of the present invention. Thus, also in an information recording medium provided with a plurality of information layers, the crystallization speed of the recording layer can be increased while suppressing a decrease in recording sensitivity, repeated rewriting properties and signal intensity. It is preferable that the first information recording medium of the present invention comprises first to N-th information layers, and is an optical information recording medium wherein the recording layer's phase can be changed between a crystalline phase and an amorphous phase by irradiation with a laser beam; that the first to N-th information layers are arranged in that order from the side from which the laser beam is incident; that at least the first information layer has the same film configuration as the information layer included in the above-described first information recording medium of the present invention; and that the first information layer comprises a first dielectric layer, a Cr-containing layer, a recording layer, a Ga-containing layer, a reflective layer and a transmittance adjusting layer arranged in that order from the side from which the laser beam is incident.

In the first information recording medium of the present invention, the Cr-containing layer further may comprise at least one element selected from Zr, Hf, Y and Si. Preferably, the Cr-containing layer comprises $Cr_2O_3$ and at least one oxide selected from $ZrO_2$, $HfO_2$, $Y_2O_3$ and $SiO_2$. It should be noted that in this case, it is preferable that the Cr content concentration in the Cr-containing layer is 5 to 40 atom %, and it is preferable that the O content concentration is 55 to 75 atom %. Moreover, it is preferable that the $Cr_2O_3$ content concentration in the Cr-containing layer is 10 to 90 mol %.

In the first information recording medium of the present invention, the Ga-containing layer further may comprise at least one element selected from Zr, Hf, Y and Si. In this case, it is preferable that the Ga-containing layer comprises a material that can be expressed by the following composition formula:

$$Ga_{A1}M_{B1}O_{100-A1-B1} \text{ (atom \%)}$$

where M is at least one element selected from Zr, Hf, Y and Si, and A1 and B1 satisfy:

$$5 < A1 < 40$$

$$2 < B1 < 30.$$

That is to say, it is preferable that the Ga content concentration in the Ga-containing layer is 5 to 40 atom %. Furthermore, it is preferable that the O content concentration is 55 to 75 atom %. In this case, the Ga-containing layer further may comprise Cr, and it is preferable that it contains 3 to 25 atom % Cr.

In the first information recording medium according to the present invention, it is preferable that the Ga-containing layer comprises $Ga_2O_3$ and at least one oxide selected from $ZrO_2$, $HfO_2$, $Y_2O_3$ and $SiO_2$. In this case, it is preferable that the Ga-containing layer comprises a material that can be expressed by the following composition formula:

$$(Ga_2O_3)_{C1}(Z1)_{100-C1} \text{ (mol \%)} \qquad (2)$$

where Z1 is at least one oxide selected from $ZrO_2$, $HfO_2$, $Y_2O_3$ and $SiO_2$, and C1 satisfies:

$$10 \leq C1 \leq 90.$$

That is to say, it is preferable that the $Ga_2O_3$ content concentration in the Ga-containing layer is 10 to 90 mol %. In this case, the Ga-containing layer further may comprise $Cr_2O_3$, preferably in a content of 5 to 40 mol %.

If the second information recording medium is an optical information recording medium wherein the recording layer's phase can be changed between the crystalline phase and the amorphous phase by irradiation with a laser beam, then it is preferable that the first Ga-containing layer, the recording layer and the second Ga-containing layer are arranged in this order from a side from which the laser beam is incident, and that the information layer further comprises at least one of a first dielectric layer arranged closer to the side from which the laser beam is incident than the first Ga-containing layer, and a second dielectric layer arranged further away from the side from which the laser beam is incident than the second Ga-containing layer. Moreover, the information layer further may comprise a reflective layer arranged further away from the side from which the laser beam is incident than the second Ga-containing layer. By providing at least one of the first and the second dielectric layers or the reflective layer, the effect of increasing the optical absorption efficiency of the recording layer or the signal intensity or the like can be attained as well.

The second information recording medium according to the present invention also may be a multi-layer information recording medium comprising first to N-th information layers (where N is an integer of 2 or more). In this case, it is preferable that at least one of the first to N-th information layers has the same film configuration as the information layer included in the above-described second information recording medium of the present invention. Thus, also in an information recording medium provided with a plurality of information layers, the crystallization speed of the recording layer can be increased while suppressing a decrease in recording sensitivity, repeated rewriting properties and signal intensity. It is preferable that the second information recording medium of the present invention comprises first to N-th information layers, and is an optical information recording medium wherein the recording layer's phase can be changed between a crystalline phase and an amorphous phase by irradiation with a laser beam; that the first to N-th information layers are arranged in that order from the side from which the laser beam is incident; that at least the first information layer has the same film configuration as the information layer included in the above-described second information recording medium of the present invention; and that the first information layer comprises a first dielectric layer, the first Ga-containing layer, the recording layer, the second Ga-containing layer, a reflective layer and a transmittance adjusting layer arranged in that order from the side from which the laser beam is incident.

In the second information recording medium of the present invention, at least one of the first Ga-containing layer and the second Ga-containing layer further may comprise at least one element selected from Zr, Hf, Y and Si. In this case, it is preferable that at least one of the first Ga-containing layer and the second Ga-containing layer comprises a material that can be expressed by the composition formula (1), and that A1 and B1 satisfy 5<A1<40 and 2<B1<30. That is to say, it is preferable that the Ga content concentration in the first and/or second Ga-containing layer is 5 to 40 atom %. It is also preferable that the O content concentration in this case is 55 to 75%. Also, in this case, the Ga-containing layers further may comprise Cr, preferably at a content of 3 to 25%.

In the second information recording medium according to the present invention, it is preferable that at least one of the first Ga-containing layer and the second Ga-containing layer comprise $Ga_2O_3$ and at least one oxide selected from $ZrO_2$, $HfO_2$, $Y_2O_3$ and $SiO_2$. In this case, it is preferable that at least one of the first Ga-containing layer and the second Ga-containing layer comprises a material that can be expressed by the composition formula (2), and that $10 \leq C1 \leq 90$. That is to say, it is preferable that the $Ga_2O_3$ content concentration in the first and/or the second Ga-containing layer is 10 to 90 mol %. In this case, the first Ga-containing layer or the second Ga-containing layer further may comprise $Cr_2O_3$, preferably at a content of 5 to 40 mol %.

If the third information recording medium is an optical information recording medium wherein the recording layer's phase can be changed between the crystalline phase and the amorphous phase by irradiation with a laser beam, then it is preferable that the first Cr-containing layer, the recording layer, the second Cr-containing layer and the Ga-containing layer are arranged in this order from a side from which the laser beam is incident, and that the information layer further comprises at least one of a first dielectric layer arranged closer to the side from which the laser beam is incident than the first Cr-containing layer, and a second dielectric layer arranged further away from the side from which the laser beam is incident than the second Cr-containing layer. Moreover, the information layer further may comprise a reflective layer arranged further away from the side from which the laser beam is incident than the second Cr-containing layer. By providing at least one of the first and the second dielectric layers or the reflective layer, the effect of increasing the optical absorption efficiency of the recording layer or the signal intensity or the like can be attained as well.

The third information recording medium according to the present invention also may be a multi-layer information recording medium comprising first to N-th information layers (where N is an integer of 2 or more). In this case, it is preferable that at least one of the first to N-th information layers has the same film configuration as the information layer included in the above-described third information recording medium of the present invention. Thus, also in an information recording medium provided with a plurality of information layers, the crystallization speed of the recording layer can be increased while suppressing a decrease in recording sensitivity, repeated rewriting properties and signal intensity. It is preferable that the third information recording medium of the present invention comprises first to N-th information layers, and is an optical information recording medium wherein the recording layer's phase can be changed between a crystalline phase and an amorphous phase by irradiation with a laser beam; that the first to N-th information layers are arranged in that order from the side from which the laser beam is incident; that at least the first information layer has the same film configuration as the information layer included in the above-described third information recording medium of the present invention; and that the first information layer comprises a first dielectric layer, the first Cr-containing layer, the recording layer, the second Cr-containing layer, the Ga-containing layer, a reflective layer and a transmittance adjusting layer arranged in that order from the side from which the laser beam is incident.

In the third information recording medium according to the present invention, at least one of the first Cr-containing layer and the second Cr-containing layer further may comprise at least one element selected from Zr, Hf, Y and Si. Preferably, at least one of the first Cr-containing layer and the second Cr-containing layer comprises $Cr_2O_3$ and at least one oxide selected from $ZrO_2$, $HfO_2$, $Y_2O_3$ and $SiO_2$. In this case, it is preferable that the Cr content concentration in the Cr-containing layer is 5 to 40 atom %, and the O content concentration is 55 to 75 atom %. Moreover, it is preferable that the $Cr_2O_3$ content concentration in the Cr-containing layer is 10 to 90 mol %.

In the third information recording medium according to the present invention, the Ga-containing layer further may comprise at least one element selected from Zr, Hf, Y and Si. In this case, it is preferable that the Ga-containing layer comprises a material that can be expressed by the composition formula (1), and that 5<A1<40 and 2<B1<30. That is to say, it is preferable that the Ga content concentration in the Ga-containing layer is 5 to 40 atom %. Moreover, it is preferable that the 0 content concentration in this case is 55 to 75 atom %. In this case, the Ga-containing layer further may comprise Cr, preferably at a content of 3 to 25 atom %.

It is also preferable that the Ga-containing layer comprises $Ga_2O_3$ and at least one oxide selected from $ZrO_2$, $HfO_2$, $Y_2O_3$ and $SiO_2$. In this case, it is preferable that the Ga-containing layer comprises a material that can be expressed by the composition formula (2), and C1 satisfies $10 \leq C1 \leq 90$. That is to say, it is preferable that the $Ga_2O_3$ content concentration in the Ga-containing layer is 10 to 90 mol %. In this case, the Ga-containing layer further may comprise $Cr_2O_3$, preferably at a content of 5 to 40 mol %.

If the fourth information recording medium is an optical information recording medium wherein the recording layer's phase can be changed between the crystalline phase and the amorphous phase by irradiation with a laser beam, then it is preferable that the Cr-containing layer is arranged closer to the side from which the laser beam is incident than the recording layer and the Ga-containing layer is arranged further away from the side from which the laser beam is incident than the recording layer. By arranging the Cr-containing layer and the Ga-containing layer in this way, it is possible to attain a higher recording sensitivity, signal intensity and repeated rewriting properties. Moreover, in the case of an optical information recording medium, the information layer further may comprise at least one of a first dielectric layer arranged closer to the side from which the laser beam is incident than the Cr-containing layer, and a second dielectric layer arranged further away from the side from which the laser beam is incident than the Ga-containing layer, and a reflective layer arranged further away from the side from which the laser beam is incident than the Ga-containing layer. By providing at least one of the first and the second dielectric layers and/or the reflective layer, the effect of increasing the optical absorption efficiency of the recording layer or the signal intensity or the like can be attained as well. In the fourth information recording medium, the C-containing layer is provided between the Cr-containing layer and the recording layer and/or the Ga-containing layer and the recording layer. Therefore, adhesion between the Cr-containing layer and the recording layer and/or the Ga-containing layer and the recording layer is improved, and high reliability can be attained.

The fourth information recording medium according to the present invention also may be a multi-layer information recording medium comprising first to N-th information layers (where N is an integer of 2 or more). In this case, it is preferable that at least one of the first to N-th information layers has the same film configuration as the information layer included in the above-described fourth information recording medium of the present invention. Thus, also in an information recording medium provided with a plurality of information layers, the crystallization speed of the recording layer can be increased while suppressing a decrease in recording sensitivity, repeated rewriting properties and signal intensity. It is preferable that the fourth information recording medium of the present invention comprises first to N-th information layers, and is an optical information recording medium wherein the recording layer's phase can be changed between a crystalline phase and an amorphous phase by irradiation with a laser beam; that the first to N-th information layers are arranged in that order from the side from which the laser beam is incident; that at least the first information layer has the same film configuration as the information layer included in the above-described fourth information recording medium of the present invention; and that the first information layer comprises a first dielectric arranged closer to the side from which the laser beam is incident than the Cr-containing layer, and a reflective layer and a transmittance adjusting layer arranged further away from the side from which the laser beam is incident than the Ga-containing layer.

In the fourth information recording medium of the present invention, the Ga-containing layer further may comprise at least one element selected from Zr, Hf, Y and Si. In this case, it is preferable that the Ga-containing layer comprises a material that can be expressed by the composition formula (1) and A1 and B1 satisfy 5<A1<40 and 2<B1<30. That is to say, it is preferable that the Ga content concentration in the Ga-containing layer is 5 to 40 atom %. Moreover, it is preferable that the O content concentration in this case is 55 to 75 atom %. The Ga-containing layer further may comprise Cr, preferably at a content of 3 to 25 atom %.

In the fourth information recording medium according to the present invention, it is preferable that the Ga-containing layer comprises $Ga_2O_3$ and at least one oxide selected from $ZrO_2$, $HfO_2$, $Y_2O_3$ and $SiO_2$. In this case, it is preferable that the Ga-containing layer comprises a material that can be expressed by the composition formula (2), and that C1 satisfies $10 \leq C1 \leq 90$. That is to say, it is preferable that the $Ga_2O_3$ content concentration in the Ga-containing layer is 10 to 90 mol %. The Ga-containing layer further may comprise $Cr_2O_3$, preferably at a content of 5 to 40 mol %.

The following is an explanation of first to fourth information recording medium manufacturing methods of the present invention.

With the first to fourth manufacturing methods, it is possible to manufacture the above-described first to fourth information recording media, with which the crystallization speed of the recording layer is increased while suppressing a decrease in recording sensitivity, repeated rewriting properties and signal intensity.

The Cr-containing sputtering target used in the first, third and fourth manufacturing method (in the third manufacturing method, at least one of the first Cr-containing sputtering target and the second Cr-containing sputtering target) further may comprise at least one element selected from Zr, Hf, Y and Si. It is preferable that the Cr-containing sputtering target comprises $Cr_2O_3$ and at least one oxide selected from $ZrO_2$, $HfO_2$, $Y_2O_3$ and $SiO_2$.

The Ga-containing sputtering target used in the first to fourth manufacturing methods (in the second manufacturing method, at least one of the first Ga-containing sputtering target and the second Ga-containing sputtering target) further may comprise at least one element selected from Zr, Hf, Y and Si. In this case, it is preferable that the Ga-containing sputtering target comprises a material that can be expressed by the following composition formula:

$$Ga_{A2}M1_{B2}O_{100-A2-B2} \text{ (atom \%)} \qquad (3)$$

where M1 is at least one element selected from Zr, Hf, Y and Si, and A2 and B2 satisfy $3<A2<42$ $0<B2<32.$ The Ga-containing sputtering target further may comprise Cr.

It is preferable that the Ga-containing sputtering target used in the first to fourth manufacturing methods (in the second manufacturing method, at least one of the first Ga-containing sputtering target and the second Ga-containing sputtering target) comprises $Ga_2O_3$ and at least one oxide selected from $ZrO_2$, $HfO_2$, $Y_2O_3$ and $SiO_2$. In this case, it is preferable that the Ga-containing sputtering target comprises a material that can be expressed by the following composition formula:

$$(Ga_2O_3)_{C2}(Z1)_{100-C2} \text{ (mol \%)} \qquad (4)$$

where Z1 is at least one oxide selected from $ZrO_2$, $HfO_2$, $Y_2O_3$ and $SiO_2$, and C2 satisfies:

$8 \leq C2 \leq 92.$

The Ga-containing sputtering target further may comprise $Cr_2O_3$.

The following is an explanation of embodiments of the present invention, with reference to the accompanying drawings. It should be noted that the following embodiments are mere examples, and that the present invention is not limited to these embodiments. Moreover, in the following embodiments, similar elements may be denoted by like numerals, and their further explanation may be omitted.

Embodiment 1

In Embodiment 1, an example of an information recording medium according to the present invention is explained. FIG. 1 shows a partial cross-sectional view of an information recording medium 15 according to Embodiment 1. The information recording medium 15 is an optical information recording medium on which information can be recorded and/or reproduced by irradiating a laser beam 11.

The information recording medium 15 is provided with an information layer 16 on a substrate 14, and furthermore with a transparent layer 13 on the information layer 16. In this information recording medium 15, the laser beam 11 is irradiated from the side of the transparent layer 13. The information layer 16 is made from a first dielectric layer 102, a first interface layer 103, a recording film 104, a second interface layer 105, a second dielectric layer 106 and a reflective layer 108, layered in this order from the side from which the laser beam is incident.

The transparent layer 13 is made from a dielectric or a resin, such as a light-curing resin (in particular a UV-curing resin) or a delayed action type thermosetting resin. The transparent layer 13 preferably has a small optical absorption with respect to the laser beam that is used, and preferably has a small birefringence in the short wavelength region. Furthermore, a transparent disk-shaped resin, such as polycarbonate, amorphous polyolefine or polymethylmethacrylate (PMMA), or glass may be used for the transparent layer 13. If such a material is used, then the transparent layer 13 can be glued to the information layer 16 with a resin, such as a light-curing resin (in particular a UV-curing resin) or a delayed action type thermosetting resin for example.

The wavelength $\lambda$ of the laser beam 11 determines the spot size when focusing the laser beam 11. The shorter the wavelength $\lambda$ of the laser beam 11, the smaller the spot diameter to which the laser beam 11 can be focused, so that for the case of high-density recording, it is particularly preferable that the wavelength of the laser beam 11 is not greater than 450 nm. Moreover, if the wavelength $\lambda$ is less than 350 nm, then the optical absorption by the transparent layer 13 for example is increased. Therefore, it is preferable that the wavelength $\lambda$ of the laser beam 11 is at least 350 nm. Thus, it is particularly preferable that the wavelength $\lambda$ of the laser beam 11 is in the range of 350 to 450 nm.

The substrate 14 is transparent and disk-shaped. A resin such as polycarbonate, amorphous polyolefin or PMMA, or glass may be used for the substrate 14, for example.

If necessary, guide grooves for guiding the laser beam 11 may be formed on the surface of the substrate 14 facing the information layer 16. It is preferable that the surface of the substrate 14 on the side facing away from the information layer 16 is smooth. Polycarbonate is especially advantageous as the material for the substrate 14, due to its excellent transfer properties and suitability for mass production, as well as its low cost.

It is preferable that the thickness of the substrate 14 is in the range of 0.5 mm to 1.2 mm, so that it is sufficiently strong, and the overall thickness of the information recording medium 15 becomes about 1.2 mm. It should be noted that if the thickness of the transparent layer 13 is about 0.6 mm (thickness allowing favorable recording and reproduction at a numerical aperture of NA=0.6), then it is preferable that the thickness of the substrate 14 is in the range of 0.55 mm to 0.65 mm. Moreover, if the thickness of the transparent layer 13 is about 0.1 mm (thickness allowing favorable recording and reproduction at a numerical aperture of NA=0.85), then it is preferable that the thickness of the substrate 14 is in the range of 1.05 mm to 1.15 mm.

The following is a more detailed description of the configuration of the information layer 16.

As noted above, the information layer 16 comprises a first dielectric layer 102, a first interface layer 103, a recording layer 104, a second interface layer 105, a second dielectric layer 106 and a reflective layer 108, layered in this order from the side from which the laser beam 11 is incident.

The first dielectric layer 102 is made from a dielectric material. The function of this first dielectric layer 102 is to prevent oxidation, corrosion and deformation of the recording layer 104, to adjust the optical distance in order to increase the optical absorption efficiency of the recording layer 104, and to increase the carrier level by increasing the change in the amount of reflected light before and after recording. The first dielectric layer 102 can be made using an oxide such as $TiO_2$, $ZrO_2$, $HfO_2$, $ZnO$, $Nb_2O_2$, $Ta_2O_5$, $SiO_2$, $Al_2O_3$, $Bi_2O_3$, $Cr_2O_3$, $Ga_2O_3$, or $In_2O_3$. It also can be made using a nitride, such as C—N, Ti—N, Zr—N, Nb—N, Ta—N, Si—N, Ge—N, Cr—N, Al—N, Ge—Si—N, or Ge—Cr—N. It also can be made using a sulfide, such as ZnS, a carbide, such as SiC, or a fluoride, such as $LaF_3$, or using C. Moreover, it is also possible to use a mixture of the above materials. For example, $ZnS$—$SiO_2$, which is a mixture of ZnS and $SiO_2$, is particularly excellent as the material of the first dielectric layer 102. $ZnS$—$SiO_2$ is an amorphous material, which has a high refractive index, fast film formation speed, and favorable mechanical properties and resistance against moisture.

The film thickness of the first dielectric layer 102 can be determined strictly by calculation with the matrix method, such that the condition is satisfied that the change of the reflected light amount between the crystalline phase and the amorphous phase of the recording layer 104 is large.

The function of the first interface layer 103 is to prevent the migration of substances between the first dielectric layer 102 and the recording layer 104 due to repeated recording. It is preferable that the first interface layer 103 is made of a material whose optical absorption is low, which has a melting point that is so high so that it does not melt during recording, and which has good adhesion to the recording layer 104. That it is a material whose melting point is so high that it does not melt during recording is a necessary property in order to ensure that the material of the first interface layer 102 does not melt and contaminate the recording layer 104 when a high power laser beam 11 is irradiated. The reason for this is that, if the material of the first interface layer 103 contaminates the recording layer 104, then the composition of the recording layer 104 changes, and the rewriting properties deteriorate dramatically. Moreover, that it is a material with good adhesion to the recording layer 104 is a necessary property for ensuring reliability.

Also the function of the second interface layer 105 is to prevent the migration of substances between the second dielectric layer 106 and the recording layer 104 due to repeated recording, like the first interface layer 103. Consequently, it is preferable that is made of a material having the same qualities.

The first interface layer 103 and the second interface layer 105 in this embodiment can be made using any of the following four combinations (I) to (IV):

(I) One of the first interface layer 103 and the second interface layer 105 is made of a Cr-containing layer containing at least Cr and O, and the other layer is made of a Ga-containing layer containing at least Ga and O.

(II) Both the first interface layer 103 and the second interface layer 105 are made of a Ga-containing layer containing at least Ga and O.

(III) One of the first interface layer 103 and the second interface layer 105 is made of a Cr-containing layer containing at least Cr and O, and the other layer is made of two layers, namely a Cr-containing layer containing at least Cr and O, and a Ga-containing layer containing at least Ga and O.

(IV) One of the first interface layer 103 and the second interface layer 105 is made of a Cr-containing layer containing at least Cr and O, the other layer is made of a Ga-containing layer containing at least Ga and O, and a C-containing layer containing C as its principal component further is provided between the recording layer and the Cr-containing layer and/or between the recording layer and the Ga-containing layer.

The present embodiment is explained for the case in which the first interface layer 103 and the second interface layer 105 are made with the combination (I).

In this embodiment, the first interface layer 103 is made of a material containing Cr and O or a material containing Ga and O. That is to say, the first interface layer 103 is a Cr-containing layer or a Ga-containing layer. Here, it is preferable that the Cr-containing layer includes the oxide $Cr_2O_3$ made of Cr and O. And it is preferable that the Ga-containing layer includes the oxide $Ga_2O_3$ made of Ga and O. $Cr_2O_3$ and $Ga_2O_3$ are materials having favorable adhesion to the recording layer 104, so that by including these oxides in the first interface layer 103, the adhesion to the recording layer 104 can be improved.

Other than Cr and O or Ga and O, the first interface layer 103 further may comprise M1 (where M1 is at least one element selected from Zr, Hf, Y and Si.) It is preferable that these elements are comprised as oxides, such as $ZrO_2$, $HfO_2$, $Y_2O_3$ and $SiO_2$. For example, $ZrO_2$ and $HfO_2$ are transparent, have a high melting point of about 2700 to 2800° C. and are oxide materials with comparatively low thermal conductivity. Consequently, including these oxides in the first interface layer 103 improves the repeated rewriting properties. By mixing these two oxides, an information recording medium 15 can be attained that has superior repeated rewriting properties and high reliability, even when formed in contact with the recording layer 104.

If the first interface layer 103 comprises at least one of $ZrO_2$ and $HfO_2$, then it is preferable that the content of $Cr_2O_3$ included in the $Cr_2O_3$—$ZrO_2$ or $Cr_2O_3$—$HfO_2$ or the content of $Ga_2O_3$ included in the $Ga_2O_3$—$ZrO_2$ or $Ga_2O_3$—$HfO_2$ of the first interface layer 103 is at least 10 mol %, in order to ensure the adhesion to the recording layer 104. Moreover, in order to keep the optical absorption low, it is preferable that the content of $Cr_2O_3$ included in the $Cr_2O_3$—$ZrO_2$ or $Cr_2O_3$—$HfO_2$ or the content of $Ga_2O_3$ included in the $Ga_2O_3$—$ZrO_2$ or $Ga_2O_3$—$HfO_2$ is not greater than 90 mol %.

Moreover, if the first interface layer 103 contains Si as the element M1, then it is preferable that the Si is contained in the form of an oxide, such as $SiO_2$. By including $SiO_2$, it is possible to realize an information layer 16 with superior recording capabilities, in which the transparency of the first interface layer 103 is increased. The content of $SiO_2$ in the $SiO_2$—$Cr_2O_3$ or $SiO_2$—$Ga_2O_3$ is preferably at least 10 mol % and preferably at most 90 mol %. More preferably it is at least 10 mol % and at most 40 mol %.

Moreover, if the first interface layer 103 contains Y as the element M1, then it is preferable that the Y is contained in the form of an oxide, such as $Y_2O_3$. By including $Y_2O_3$, it is possible to realize an information layer 16 with superior repeated rewriting properties. The content of $Y_2O_3$ in the $Y_2O_3$—$Cr_2O_3$ or $Y_2O_3$—$Ga_2O_3$ is preferably at least 10 mol % and preferably at most 90 mol %.

It is preferable that the film thickness of the first interface layer 103 is in the range of 0.5 nm to 15 nm, and more preferably in the range of 1 nm to 7 nm, so that the change of the amount of reflected light before and after recording in the information layer 16 due to optical absorption with the first interface layer 103 is small.

If the first interface layer 103 is a Cr-containing layer, then the second interface layer 105 is formed from a material including Ga and O. That is to say, in this case, the second interface layer 105 is made of a Ga-containing layer. It is then further preferable that the Ga-containing layer includes the oxide $Ga_2O_3$ made of Ga and O. If the first interface layer 103 is a Ga-containing layer, then the second interface layer 105 is formed from a material including Cr and O. That is to say, in this case, the second interface layer 105 is made of a Cr-containing layer. It is then further preferable that it includes the oxide $Cr_2O_3$ made of Cr and O. Like the first interface layer 103, it also may include the element M1 in addition to Cr and O or Ga and O. Since the second interface layer 105 tends to have poorer adhesion to the recording layer 104 than the first interface layer 103, it is preferable that its content of $Cr_2O_3$ and $Ga_2O_3$ is at least 20 mol %, which is higher than the content for the first interface layer 103.

Like for the first interface layer 103, is preferable that the film thickness of the second interface layer 105 is in the range of 0.5 nm to 15 nm, and even more preferably in the range of 1 nm to 7 nm.

For the second dielectric layer 106, the same material system as for the first dielectric layer 102 can be used. Of these, $Bi_2O_3$—$SiO_2$ which is a mixture of $Bi_2O_3$ and $SiO_2$, is a material that is superior as the second dielectric layer 106, because it has low thermal conductivity and does not include S.

It is preferable that the film thickness of the second dielectric layer 106 is in the range of 2 nm to 75 nm, and even more preferably in the range of 2 nm to 40 nm. By choosing the film thickness of the second dielectric layer 106 from this range, it is possible to disperse heat generated in the recording layer 104 effectively to the side of the reflective layer 108.

The material of the recording layer 104 is a material whose phase can be changed reversibly between crystalline and amorphous by irradiation with a laser beam 11. The recording layer 104 is made of a material including, for example, Ge, Te and M2 (where M2 is at least one element selected from Sb and Bi), and further may include at least one element of Ga and In. More specifically, the recording layer 104 can be made of a material expressed by $Ge_a(M2)_bTe_{3+a}$. In this material, it is preferable that $0<a \leq 60$ and more preferably $4 \leq a \leq 40$ are satisfied, so that the amorphous phase is stable, the archival characteristics at low transfer rates are good, the rise of the melting point and the decrease of the crystallization speed are low, and the archival overwrite characteristics at high transfer rates are good. Moreover, it is preferable that $1.5 \leq b \leq 7$ is satisfied and even more preferable that $2 \leq b \leq 4$ is satisfied, because then the decrease in the crystallization speed is low.

The recording layer 104 also may be made of the material $(Ge-M3)_a(M2)_bTe_{3+a}$ in which some of the Ge in $Ge_a(M2)_bTe_{3+a}$ is substituted with at least one element (M3) selected from Sn and Pb. If this material is used, then the element M3 substituting the Ge improves the crystallization capability, so that a sufficiently high erasing ratio can be attained even when the film thickness of the recording layer 104 is thin. As the element M3, Sn is more preferable, because it is non-toxic. If this material is used, it is preferable that $0<a \leq 60$ (more preferably $4 \leq a \leq 40$) and that $1.5 \leq b \leq 7$ (more preferably $2 \leq b \leq 4$).

Moreover, the recording layer 104 also may be formed from a material including Sb and M4 (where M4 is at least one element selected from V, Mn, Ga, Ge, Se, Ag, In, Sn, Te, Pb, Bi and Au), for example. More specifically, the recording layer 104 can be made of a material expressed by $Sb_x(M4)_{100-x}$ (in atom %). If x satisfies $50 \leq x \leq 95$, then the difference in the reflectances of the information recording medium 15 in the crystalline phase and the amorphous phase of the recording layer 104 can be made large, and favorable recording/reproducing properties can be attained. In particular if x satisfies $75 \leq x \leq 95$, then the crystallization speed is particularly fast, and favorable rewriting properties at high transfer rates are attained. Moreover, if x satisfies $50 \leq x \leq 75$, then the amorphous phase is particularly stable, and favorable recording properties at low transfer rates are attained.

It is preferable that the film thickness of the recording layer 104 is in the range of 6 nm to 15 nm, in order to ensure a high recording sensitivity of the information layer 16. Also, within this range, when the recording layer 104 is thick, the thermal influence on adjacent regions due to diffusion of heat in the in-plane direction becomes large. If the recording layer 104 is thin, then the reflectance of the information layer 16 becomes small. Thus, it is more preferable that the film thickness of the recording layer 104 is in the range of 8 nm to 13 nm.

The reflective layer 108 has the optical function increasing the amount of light that is absorbed by the recording layer 104. The reflective layer 108 also has the thermal function to quickly diffuse heat that is generated in the recording layer 104, and to make the amorphization of the recording layer 104 easier. Furthermore, the reflective layer 108 also has the function of protecting the multi-layer film from the environment in which it is used.

As the material of the reflective layer 108, it is possible to use a single metal with a high thermal conductivity, such as Ag, Au, Cu or Al. It is also possible to use an alloy, such as Al—Cr, Al—Ti, Au—Pd, Au—Cr, Ag—Pd, Ag—Pd—Cu, Ag—Pd—Ti, Ag—Ru—Au, Ag—Cu—Ni, Ag—Zn—Al, Ag—Nd—Au, Ag—Nd—Cu or Cu—Si. In particular Ag alloys have a high thermal conductivity, so that they are preferable as the material for the reflective layer 108. It is preferable that the film thickness of the reflective layer 108 is at least 30 nm, to attain sufficient heat diffusion. Within this range, if the reflective layer 108 is thicker than 200 nm, then its heat diffusion becomes too large, so that the recording sensitivity of the information layer 16 decreases. Consequently, it is more preferable that the film thickness of the recording layer 108 is in the range of 30 nm to 200 nm.

It is also possible further to provide a low thermal conductivity layer made of a material with lower thermal conductivity than the reflective layer 108 between the reflective layer 108 and the second dielectric layer 106. In this case, the low thermal conductivity layer can be formed using a material that has a lower thermal conductivity than the above-noted material of the reflective layer 108. For example, if an Ag alloy is used for the reflective layer 108, then it is possible to use Al or an Al alloy for this low thermal conductivity layer. The low thermal conductivity layer can be made using Cr, Ni, Si or C or the like alone, or using an oxide such as $TiO_2$, $ZrO_2$, $HfO_2$, ZnO, $Nb_2O_5$, $Ta_2O_5$, $SiO_2$, $SnO_2$, $Al_2O_3$, $Bi_2O_3$, $Cr_2O_3$ or $Ga_2O_3$. It also can be made using a nitride, such as C—N, Ti—N, Zr—N, Nb—N, Ta—N, Si—N, Ge—N, Cr—N, Al—N, Ge—Si—N, or Ge—Cr—N. It also can be made using a sulfide, such as ZnS, a carbide, such as SiC, or a fluoride, such as $LaF_3$. Moreover, it is also possible to use a mixture of the above materials. It is preferable that the film thickness of the low thermal conductivity layer is in the range of 3 nm to 100 nm (more preferably 10 nm to 50 nm).

It is preferable that reflectance Rc (%) of the information layer 16 when the recording layer 104 is in the crystalline phase and the reflectance Ra (%) when the recording layer 104 is in the amorphous phase satisfy Ra<Rc. Thus, the reflectance is higher in the initial state, in which no information has been recorded, than in the state in which information has been recorded, and a stable recording/reproducing operation can be accomplished. Moreover, it is preferable that Rc and Ra satisfy $0.2 \leq Ra \leq 10$ and $12 \leq Rc \leq 40$, more preferably $0.2 \leq Ra \leq 5$ and $12 \leq Rc \leq 30$, so that the difference (Rc−Ra) of the reflectances is large, and favorable recording/reproducing properties can be attained.

The information recording medium 15 can be manufactured by the method explained below.

First, the information layer 16 is formed on the substrate 14 (whose thickness is, for example, 1.1 mm). The information layer 16 is made of a multi-layer film, and the layers are formed in a film-forming device by sputtering in order with sputtering targets of the corresponding materials.

More specifically, first, the reflective layer 108 is formed on the substrate 14. The reflective layer 108 can be formed by sputtering with a sputtering target made of the metal or alloy serving as the reflective layer 108, in an Ar gas atmosphere or a mixed gas atmosphere made of Ar gas and a reactive gas (at least one gas selected from oxygen gas and nitrogen gas).

Subsequently, a low thermal conductivity layer is formed on the reflective layer 108, if necessary. The low thermal conductivity layer can be formed by sputtering with a sputtering target made of the element or compound constituting the low thermal conductivity layer, in an Ar gas atmosphere or a mixed gas atmosphere of Ar gas and a reactive gas.

Subsequently, the second dielectric layer 106 is formed on the reflective layer 108 (or on the low thermal conductivity layer if a low thermal conductivity layer has been formed). The second dielectric layer 106 can be formed by sputtering with a sputtering target made of the compound constituting the second dielectric layer 106, in an Ar gas atmosphere or a mixed gas atmosphere of Ar gas and a reactive gas. Moreover, the second dielectric layer 106 also can be formed by reactive sputtering with a sputtering target made of a metal including the element constituting the second dielectric layer 106, in a mixed gas atmosphere made of Ar gas and a reactive gas.

Subsequently, the second interface layer 105 is formed on the second dielectric layer 106. The second interface layer 105 can be formed on the second dielectric layer 106 by sputtering with a sputtering target made from the compound constituting the second interface layer 105 (a Cr-containing sputtering target containing Cr and O if the second interface layer 105 is made of a Cr-containing layer, or a Ga-containing sputtering target if the second interface layer 105 is made of a Ga-containing layer), in an Ar gas atmosphere or a mixed gas atmosphere of Ar gas and a reactive gas.

Subsequently, the recording layer 104 is formed on the second interface layer 105. Depending on its composition, the recording layer 104 can be made by sputtering with a sputtering target made of a Ge—Te-M2 alloy, a sputtering target made of a Ge-M3-Te-M2 alloy or a sputtering target made of a Sb-M4 alloy, using one power source.

For the sputtering gas atmosphere when forming the recording layer 104, it is possible to use Ar gas, Kr gas, a mixed gas of Ar gas and reactive gas, or a mixed gas of Kr gas and reactive gas. Moreover, the recording layer 104 also can be formed by simultaneous sputtering with sputtering targets made of the necessary elementary metals selected from Ge, Te, M2, M3, Sb and M4, using a plurality of power sources. Moreover, the recording layer 104 also can be formed by simultaneous sputtering with binary or ternary sputtering targets or the like combining the necessary elements selected from Ge, Te, M2, M3, Sb and M4, using a plurality of power sources. Also in these cases, it is possible to perform the sputtering in an Ar gas atmosphere, a Kr gas atmosphere, a mixed gas atmosphere of Ar gas and reactive gas, or a mixed gas atmosphere of Kr gas and reactive gas.

Subsequently, the first interface layer 103 is formed on the recording layer 104. The first interface layer 103 can be formed by sputtering with a sputtering target made from the compound constituting the first interface layer 103 (a Cr-containing sputtering target containing Cr and O if the first interface layer 103 is made of a Cr-containing layer, or a Ga-containing sputtering target if the first interface layer 103 is made of a Ga-containing layer), in an Ar gas atmosphere or a mixed gas atmosphere of Ar gas and a reactive gas.

Subsequently, the first dielectric layer 102 is formed on the first interface layer 103. The first dielectric layer 102 is formed by sputtering with a sputtering target made of the compound constituting the first dielectric layer 102, in an Ar gas atmosphere or a mixed gas atmosphere of Ar gas and a reactive gas. Moreover, the first dielectric layer 102 also can be formed by reactive sputtering with a sputtering target made of a metal including the element constituting the first dielectric layer 102, in a mixed gas atmosphere made of Ar gas and a reactive gas.

Lastly, the transparent layer 13 is formed on the first dielectric layer 102. The transparent layer 13 can be made by spin-coating a light-curing resin (in particular a UV-curing resin) or a delayed action type thermosetting resin on the first dielectric layer 102, and then curing the resin. Furthermore, a transparent disk-shaped resin, such as polycarbonate, amorphous polyolefin or PMMA, or a glass substrate or the like may be used for the transparent layer 13. In this case, the transparent layer 13 can be formed by first applying a resin such as a light-curing resin (in particular a UV-curing resin) or a delayed action type thermosetting resin on the first dielectric layer 102, adhering the substrate to the first dielectric layer 102 and spin-coating, followed by curing the resin. Moreover, it is also possible to adhere to the first dielectric layer 102 a substrate to which an adhesive resin has been applied uniformly beforehand.

It should be noted that, if necessary, it is also possible to perform an initialization step of crystallizing the entire recording layer 104, after the first dielectric layer 102 has been formed or after the transparent layer 13 has been formed. The crystallization of the recording layer 104 can be performed by irradiating a laser beam.

Thus, the information recording medium 15 can be manufactured as described above. It should be noted that in this embodiment, sputtering was used as the film forming method for each of the layers, but there is no limitation to this, and it is also possible to use such methods as vacuum vapor deposition, ion plating, CVD (Chemical Vapor Deposition), MBE (Molecular Beam Epitaxy) or the like.

Embodiment 2

Figure 2:
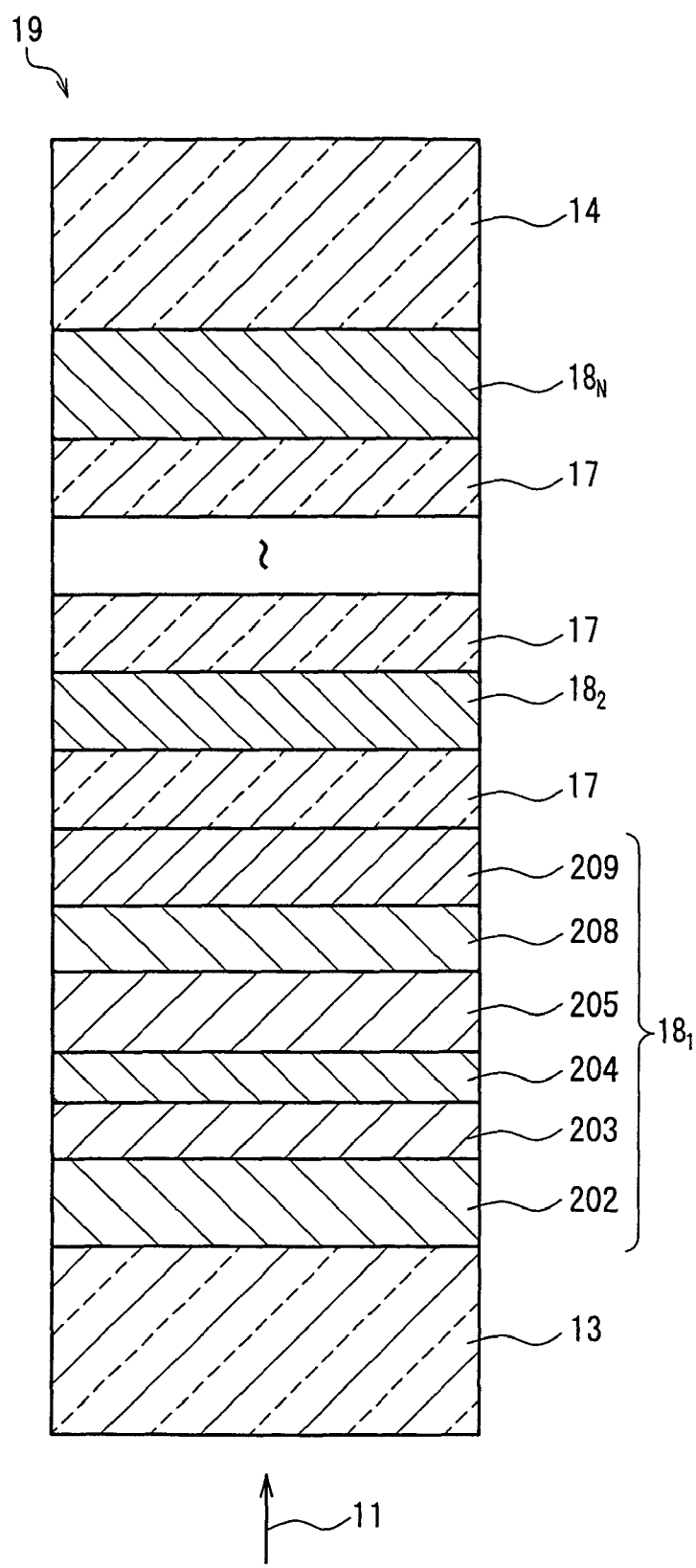
FIG. 2 is a partial cross-sectional view showing the configuration of an information recording medium according to Embodiment 2 of the present invention.

In Embodiment 2, an example of an information recording medium according to the present invention is explained. FIG. 2 shows a partial cross-sectional view of an information recording medium 19 according to Embodiment 2. The information recording medium 19 is an optical information recording medium with a multi-layer structure (referred to as "multi-layer optical information recording medium" in the following), which includes a plurality of information layers, and which can record and reproduce information on these information layers by irradiating a laser beam 11 from one side.

The information recording medium 19 is provided with a substrate 14 and, formed thereon, N (N being an integer satisfying N≧2) information layers (N-th information layer $18_N$, ..., second information layer $18_2$, first information layer $18_1$) that are layered with optical separation layers 17 formed between them, and a transparent layer 13 formed on the first information layer $18_1$. It should be noted that in this specification, the first information layer counted from the side from which the laser beam 11 is incident is referred to as "first information layer $18_1$", and the N-th information layer is referred to as "N-th information layer $18_N$". Here, the information layers up to the (N-1)th information layer counting from the side from which the laser beam 11 is irradiated have optical transparency, in order to let the laser beam 11 reach the N-th information layer $18_N$, which is arranged furthest away from the side from which the laser beam 11 is irradiated. For the substrate 14 and the transparent layer 13, it is possible to use a similar material as explained for Embodiment 1. Also the shape and function of the substrate 14 and the transparent layer 13 are the same as the shape and function described in Embodiment 1.

The optical separation layers 17 are made from a dielectric or a resin, such as a light-curing resin (in particular a UV-curing resin) or a delayed action type thermosetting resin. The optical separation layers 17 preferably have a small optical absorption with respect to the laser beam 11 that is used, and preferably have a small optical birefringence in the short wavelength region.

The optical separation layers 17 are provided in order to differentiate the respective focus positions of the first information layer $18_1$, the second information layer $18_2$, ..., to the N-th information layer $18_N$ of the information recording medium 19. The thickness of the optical separation layer 17 should be at least the focus depth ($\Delta Z$), which is determined by the numerical aperture (NA) of the objective lens and the wavelength ($\lambda$) of the laser beam 11. If the standard optical intensity of the focus is assumed to be 80% for the case that there are no aberrations, then the focus depth ($\Delta Z$) can be approximated by $\Delta Z = \lambda / \{2(NA)^2\}$. If $\lambda = 405$ nm and NA=0.85, then $\Delta Z = 0.280$ μm, and distances within ±0.3 μm are within the focus depth. Thus, in this case, the thickness of the optical separation layers 17 should be set to at least 0.6 μm. Moreover, it is desirable that the distances between the information layers are set such that the laser light can be focused using the objective lens. Consequently, it is preferable that the total thickness of the optical separation layers 17 is within the tolerance (e.g. not greater than 50 μm) allowed by the objective lens.

If necessary, guide grooves for guiding the laser beam 11 may be formed on the surface of the optical separation layers 17 on the side where the laser beam 11 is incident.

In this case, it is possible to record or reproduce the K-th information layer (where K is an integer with 1<K≦N) with a laser beam 11 that has passed through the first to (K−1)th information layer by only irradiating the laser beam 11 from one side.

It should be noted that any of the first to N-th information layers may be a read-only (ROM) information layer or a write-once (WO) information layer that can be written only once.

The following is a more detailed description of the configuration of the first information layer $18_1$.

The first information layer $18_1$ comprises a first dielectric layer 202, a first interface layer 203, a recording layer 204, a second interface layer 205, a reflective layer 208, and a transmittance adjusting layer 209, layered in this order from the side from which the laser beam 11 is incident.

The first dielectric layer 202 can be made of the same material as the first dielectric layer 102 described in Embodiment 1 (see FIG. 1), and has the same function.

The film thickness of the first dielectric layer 202 can be determined strictly by calculation with the matrix method, such that the following conditions are satisfied: the change of the reflected light amount between the crystalline phase and the amorphous phase of the recording layer 204 is large, the optical absorption at the recording layer 204 is large, and the transmittance of the first information layer $18_1$ is large.

For the first interface layer 203, it is possible to use the same material as for the first interface layer 103 described in Embodiment 1. Also, the function and shape are the same as for the first interface layer 103 of Embodiment 1.

For the second interface layer 205, it is possible to use the same material systems as for the second interface layer 105 described in Embodiment 1. It is preferable that the film thickness of the second interface layer 205 is in the range of 0.5 nm to 75 nm, and more preferably in the range of 1 nm to 40 nm. By choosing the film thickness of the second interface layer 205 from this range, it is possible to disperse heat generated in the recording layer 204 effectively to the side of the reflective layer 208.

It should be noted that it is also possible to arrange a further dielectric layer (second dielectric layer) between the second interface layer 205 and the reflective layer 208. For this second dielectric layer, the same material system as for the first dielectric layer 202 can be used. Of these, in particular a material including Ga and O is used preferably.

The recording layer 204 can be formed using the same material as for the recording layer 104 described in Embodiment 1.

The first information layer $18_1$ should have a high transmittance, in order to let the necessary amount of laser light reach the information layers that are located further away from the side from which the laser beam 11 is incident than the first information layer $18_1$ when recording or reproducing those layers. Thus, it is more preferable that the film thickness of the recording layer 204 is not greater than 9 nm, and more preferably in the range of 2 nm to 8 nm.

The reflective layer 208 has the optical function of increasing the amount of light that is absorbed by the recording layer 204. The reflective layer 208 also has the thermal function of quickly diffusing heat that is generated in the recording layer 204, and to allow easier amorphization of the recording layer 204. Furthermore, the reflective layer 208 also has the function of protecting the multi-layer film from the environment in which it is used.

For the material of the reflective layer 208, it is possible to use the same material as for the reflective layer 108 in Embodiment 1. Moreover, also its function is the same as for the reflective layer 108 in Embodiment 1. In particular Ag alloys have high thermal conductivity, so that they are preferable as the material for the reflective layer 208. It is preferable that the film thickness of the reflective layer 208 is in the range of 3 nm to 15 nm, more preferably in the range of 8 nm to 12 nm, in order to increase the transmittance of the first information layer $18_1$ as much as possible. By setting the film thickness of the reflective layer 208 to this range, the reflective layer 208 has sufficient heat diffusion capability, a sufficient reflectance of the first information layer $18_1$ can be ensured, and also the transmittance of the first information layer $18_1$ is sufficient.

The transmittance adjusting layer 209 is made of a dielectric material, and has the function of adjusting the transmittance of the first information layer $18_1$. With this transmittance adjusting layer 209, it is possible to increase both the transmittance Tc (%) of the first information layer $18_1$ when the recording layer 204 is in the crystalline phase and the transmittance Ta (%) of the first information layer $18_1$ when the recording layer 204 is in the amorphous phase. More specifically, with the first information layer $18_1$ including the transmittance adjusting layer 209, the transmittances Tc and Ta are increased by 2% to 10% compared to the case that no transmittance adjusting layer 209 is provided. Moreover, the transmittance adjusting layer 209 also has the function of effectively dispersing the heat generated in the recording layer 204.

It is preferable that the refractive index n and the extinction coefficient k of the transmittance adjusting layer 209 satisfy $2.0 \leq n$ and $k \leq 0.1$, more preferably $2.4 \leq n \leq 3.0$ and $k \leq 0.05$, in order to increase the effect of augmenting the transmittances Tc and Ta of the first information layer $18_1$.

It is preferable that the film thickness d of the transmittance adjusting layer 209 is within the range of $(1/32)\lambda/n \leq d \leq (3/16)\lambda/n$ or $(17/32)\lambda/n \leq d \leq (11/16)\lambda/n$, and more preferably within the range of $(1/16)\lambda/n \leq d \leq (5/32)\lambda/n$ or $(9/16)\lambda/n \leq d \leq (21/32)\lambda/n$. It should be noted that it is preferable that when the wavelength $\lambda$ of the laser beam 11 and the refractive index n of the transmittance adjusting layer 209 are set to, for example, 350 nm $\leq \lambda \leq$ 450 nm and $2.0 \leq n \leq 3.0$, then it is preferable that the film thickness d is in the range of 3 nm $\leq d \leq$ 40 nm or 60 nm $\leq d \leq$ 130 nm, and more preferably in the range of 7 nm $\leq d \leq$ 30 nm or 65 nm $\leq d \leq$ 120 nm. By choosing d from these ranges, both transmittances Tc and Ta of the first information layer $18_1$ can be augmented.

The transmittance adjusting layer 209 can be made using an oxide such as $TiO_2$, $ZrO_2$, $HfO_2$, $ZnO$, $Nb_2O_5$, $Ta_2O_5$, $SiO_2$, $Al_2O_3$, $Bi_2O_3$, $Cr_2O_3$, or Si—O. It also can be made using a nitride, such as Ti—N, Zr—N, Nb—N, Ta—N, Si—N, Ge—N, Cr—N, Al—N, Ge—Si—N, or Ge—Cr—N. It is also possible to use a sulfide, such as ZnS. Moreover, it is also possible to use a mixture of the above materials. Of these, in particular $TiO_2$ or a material including $TiO_2$ is used preferably. These materials have a high refractive index (n=2.6 . . . 2.8) and a low extinction coefficient (k=0.0 . . . 0.05), so that the effect of augmenting the transmittance of the first information layer $18_1$ is large.

It is preferable that the transmittances Tc and Ta of the first information layer $18_1$ satisfy $40<Tc$ and $40<Ta$, more preferably $46<Tc$ and $46<Ta$, so that the necessary amount of laser light reaches the second to N-th information layers $18_2$ to $18_N$ when recording or reproducing.

It is preferable that the transmittances Tc and Ta of the first information layer $18_1$ satisfy $-5 \leq (Tc-T1) \leq 5$, more preferably $-3 \leq (Tc-Ta) \leq 3$. When transmittances Tc and Ta satisfy this condition, then changes in the transmittances due to the state of the recording layer 204 in the first information layer $18_1$ have little influence when recording or reproducing information in the second to N-th information layers $18_2$ to $18_N$ that are arranged further away from the side on which the laser beam 11 is incident than the first information layer $18_1$, so that favorable recording and reproducing properties can be attained.

It is preferable that the reflectance $R_{c1}$ (%) of the first information layer $18_1$ when the recording layer 204 is crystalline and the reflectance $R_{a1}$ (%) of the first information layer $18_1$ when the recording layer 204 is amorphous satisfy the relation $R_{a1} < R_{c1}$. Thus, the reflectance is higher in the initial state, in which no information has been recorded, than in the state in which information has been recorded, and a stable recording/reproducing operation can be accomplished. Moreover, it is preferable that $R_{c1}$ and $R_{a1}$ satisfy $0.1 \leq R_{a1} \leq 5$ and $4 \leq R_1 \leq 15$, more preferably $0.1 \leq R_{a1} \leq 3$ and $4 \leq R_{c1} \leq 10$, so that the reflectance difference $(R_{c1} - R_{a1})$ is large and favorable recording and reproducing properties can be attained.

The information recording medium 19 can be manufactured by the method explained below.

First, (N−1) layers, namely the N-th information layer $18_N$ to the second information layer $18_2$ are formed in order on the substrate 14 (which has a thickness of, for example, 1.1 mm), with optical separation layers 17 interposed in between. The information layers are made of single-layer films or multi-layer film, and the layers can be formed in a film-forming device by sputtering in order with sputtering targets of the corresponding materials. The optical separation layers 17 can be formed by applying a light-curing resin (in particular a UV-curing resin) or a delayed action type thermosetting resin on the information layers, and then uniformly spreading the resin by rotating the entire disk (spin-coating), and then curing the resin. It should be noted that if guide grooves for the laser beam 11 are formed in the optical separation layers 17, then it is possible to form optical separation layers 17 in which predetermined guide grooves are formed in the surface by adhering a transfer substrate (mold) whose surface is provided with grooves of predetermined shape with an uncured resin, spin-coating by rotating the substrate 14 and the transfer substrate, curing the resin, and stripping transfer substrate from the cured resin.

Thus, a disk with (N−1) information layers (N-th information layer to second information layer) layered on the substrate 14, and an optical separation layer 17 formed on the second information layer $18_2$ is provided.

Subsequently, the first information layer $18_1$ is formed on the optical separation layer 17. More specifically, first, the substrate 14 on which the (N−1) information layers and the optical separation layers 17 have been formed is placed in a film-forming device, and then a transmittance adjusting layer 209 is formed on the uppermost optical separation layer 17. The transmittance adjusting layer 209 is formed by sputtering with a sputtering target made of the compound constituting the transmittance adjusting layer 209, in an Ar gas atmosphere or a mixed gas atmosphere of Ar gas and a reactive gas. Moreover, the transmittance adjusting layer 209 also can be formed by reactive sputtering using a sputtering target made of the metal constituting the transmittance adjusting layer 209, in a mixed gas atmosphere of Ar gas and a reactive gas.

Subsequently, the reflective layer 208 is formed on the transmittance adjusting layer 209. The reflective layer 208 can be formed by the same method as the reflective layer 108 described in Embodiment 1.

If a second dielectric layer is provided between the reflective layer 208 and the second interface layer 205, then this second dielectric layer is formed on the reflective layer 208. The second dielectric layer can be formed by the same method as the second dielectric layer 106 described in Embodiment 1.

Subsequently, the second interface layer 205 is formed on the reflective layer 208 (or on the second dielectric layer if a second dielectric layer is provided). The second interface layer 205 can be formed by the same method as the second interface layer 105 described in Embodiment 1.

Subsequently, the recording layer 204 is formed on the second interface layer 205. The recording layer 204 can be formed by the same method as the recording layer 104 described in Embodiment 1, using a sputtering target with the corresponding composition.

Subsequently, the first interface layer 203 is formed on the recording layer 204. The first interface layer 203 can be formed by the same method as the first interface layer 103 in Embodiment 1.

Subsequently, the first dielectric layer 202 is formed on the first interface layer 203. The first dielectric layer 202 can be formed by the same method as the first dielectric layer 102 described in Embodiment 1.

Lastly, the transparent layer 13 is formed on the first dielectric layer 202. The transparent layer 13 can be formed by the method described in Embodiment 1.

It should be noted that it is also possible to perform an initialization step of crystallizing the entire recording layer 204, after the first dielectric layer 202 has been formed or after the transparent layer 13 has been formed. The crystallization of the recording layer 204 can be performed by irradiating a laser beam.

Thus, the information recording medium 19 can be manufactured as described above. It should be noted that in this embodiment, sputtering was used as the film forming method for each of the layers, but there is no limitation to this, and it is also possible to use such methods as vacuum vapor deposition, ion plating, CVD, or MBE or the like.

Embodiment 3

Figure 3:
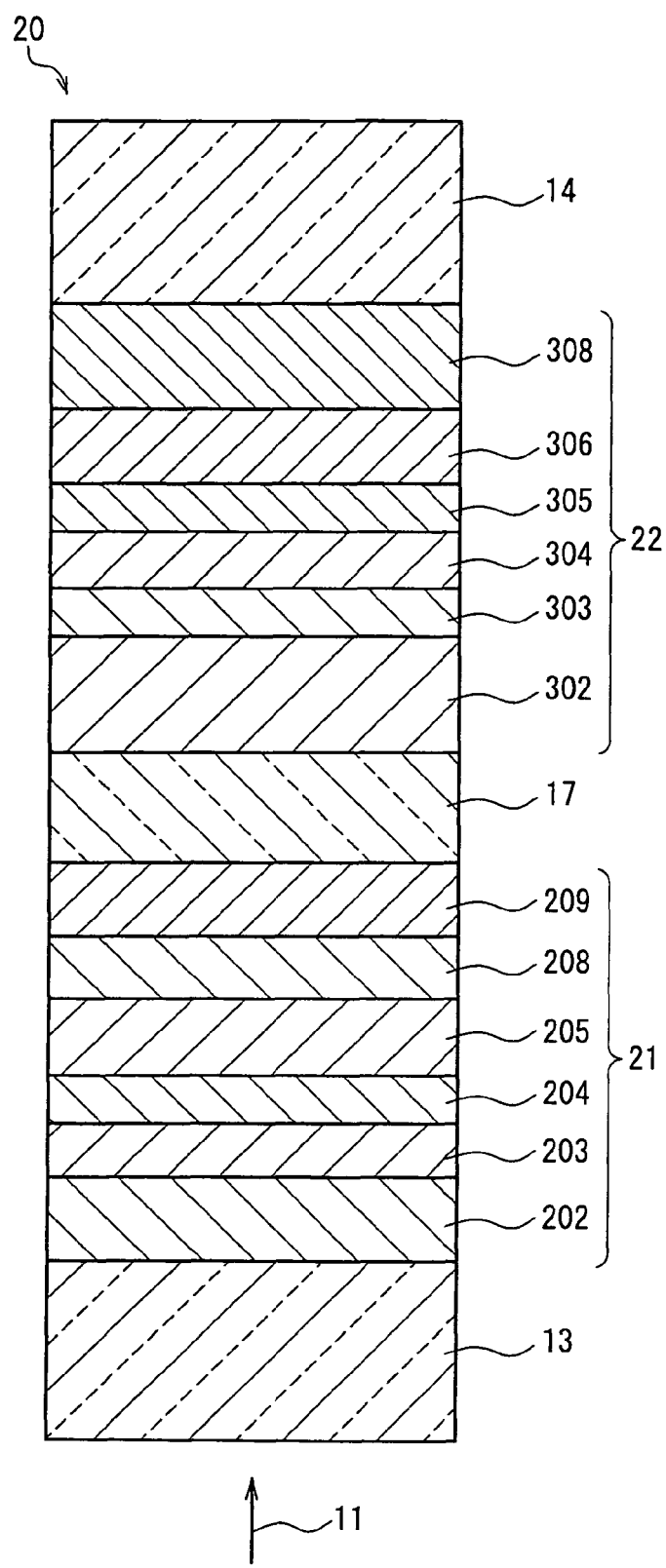
FIG. 3 is a partial cross-sectional view showing the configuration of an information recording medium according to Embodiment 3 of the present invention.

In Embodiment 3, an example of an information recording medium is explained, in which the multi-layer optical information recording medium in Embodiment 2 is provided with two information layers, that is, N=2. FIG. 3 shows a partial cross-sectional view of an information recording medium 20 according to Embodiment 3. The information recording medium 20 is a two-layer optical information recording medium in which information can be recorded or reproduced on the information layers by irradiating a laser beam 11 from one side.

The information recording medium 20 is made of a substrate 14, and a second information layer 22, an optical separation layer 17, a first information layer 21 and a transparent layer 13 layered in this order on the substrate 14. For the substrate 14, the optical separation layer 17 and the transparent layer 13, it is possible to use the same materials as explained for Embodiments 1 and 2. Also their shape and function are the same as the shape and function described in Embodiments 1 and 2. Like the first information layer $18_1$ described in Embodiment 2, the first information layer 21 is formed by layering a first dielectric layer 202, a first interface layer 203, a recording layer 204, a second interface layer 205, a reflective layer 208 and a transmittance adjusting layer 209 in this order from the side from which the laser beam 11 is incident.

The following is a more detailed description of the configuration of the second information layer 22.

The second information layer 22 comprises a first dielectric layer 302, a first interface layer 303, a recording layer 304, a second interface layer 305, a second dielectric layer 306, and a reflective layer 308, layered in this order from the side from which the laser beam 11 is incident. Recording and reproduction of the second information layer 22 can be performed with a laser beam 11 that has passed through the transparent layer 13, the first information layer 21 and the optical separation layer 17.

For the first dielectric layer 302, the same material as for the first dielectric layer 102 (see FIG. 1) described in Embodiment 1 can be used, and it also has the same function and shape.

The film thickness of the first dielectric layer 302 can be determined strictly by calculation with the matrix method, such that the condition is satisfied so that the change of the reflected light amount between the crystalline phase and the amorphous phase of the recording layer 304 is large.

For the first interface layer 303, the same material as for the first interface layer 103 described in Embodiment 1 can be used, and it also has the same function and shape.

For the second interface layer 305, the same material as for the second interface layer 105 described in Embodiment 1 can be used, and it also has the same function and shape.

For the second dielectric layer 306, the same material as for the second dielectric layer 106 described in Embodiment 1 can be used, and it also has the same function and shape.

The recording layer 304 can be formed using the same material as for the recording layer 104 described in Embodiment 1. It is preferable that the film thickness of the recording layer 304 is in the range of 6 nm to 15 nm, in order to ensure a high recording sensitivity of the second information layer 22. Also, within this range, when the recording layer 304 is thick, the thermal influence on adjacent regions due to diffusion of heat in the in-plane direction becomes large. If the recording layer 304 is thin, then the reflectance of the second information layer 25 becomes small. Thus, it is more preferable that the film thickness of the recording layer 304 is in the range of 8 nm to 13 nm.

For the reflective layer 308, the same material as for the reflective layer 108 described in Embodiment 1 can be used, and it also has the same function and shape.

As in Embodiment 1, it is also possible to provide a low thermal conductivity layer made of a material with lower thermal conductivity than the reflective layer 308 between the reflective layer 308 and the second dielectric layer 306. The materials that can be used for such a low thermal conductivity layer are as explained in Embodiment 1, and also its film thickness is as explained in Embodiment 1.

The information recording medium 20 can be manufactured by the method explained below.

First, the second information layer 22 is formed. More specifically, first, the substrate 14 (having a thickness of, for example, 1.1 mm) is prepared, and placed in a film-forming device.

Subsequently, the reflective layer 308 is formed on the substrate 14. If guide grooves for guiding the laser beam 11 are formed in the substrate 14, then the reflective layer 308 is formed on the side on which the guide grooves are formed. The reflective layer 308 can be formed by the same method as the reflective layer 108 described in Embodiment 1.

Subsequently, a low thermal conductivity layer is formed on the reflective layer 308, if necessary. The method for forming the low thermal conductivity layer is as explained in Embodiment 1.

Subsequently, the second dielectric layer 306 is formed on the reflective layer 308 (or on the low thermal conductivity layer if a low thermal conductivity layer has been formed). The second dielectric layer 306 can be formed by the same method as the second dielectric layer 106 described in Embodiment 1.

Subsequently, the second interface layer 305 is formed on the second dielectric layer 306. The second interface layer 305 can be formed by the same method as the second interface layer 105 described in Embodiment 1.

Subsequently, the recording layer 304 is formed on the second interface layer 305. The recording layer 304 can be formed by the same method as the recording layer 104 described in Embodiment 1, using a sputtering target with the corresponding composition.

Subsequently, the first interface layer 303 is formed on the recording layer 304. The first interface layer 303 can be formed by the same method as the first interface layer 103 in Embodiment 1.

Subsequently, the first dielectric layer 302 is formed on the first interface layer 303. The first dielectric layer 302 can be formed by the same method as the second dielectric layer 106 described in Embodiment 1.

Thus, the second information layer 22 is formed.

Subsequently, the optical separation layer 17 is formed on the first dielectric layer 302 of the second information layer 22. The optical separation layer 17 can be made by applying and spin-coating a light-curing resin (in particular a UV-curing resin) or a delayed action type thermosetting resin on the first dielectric layer 302, and then curing the resin. It should be noted that if the optical separation layer 17 is provided with guide grooves for the laser beam 11, then it is possible to form guide grooves in the surface by adhering with an uncured resin a transfer substrate (mold) whose surface is provided with grooves, spin-coating by rotating the substrate 14 and the transfer substrate, curing the resin, and then stripping the transfer substrate from the resin.

It should be noted that it is also possible to perform an initialization step of crystallizing the entire recording layer 304, after the first dielectric layer 302 has been formed or after the optical separation layer 17 has been formed. The crystallization of the recording layer 304 can be performed by irradiating a laser beam.

Subsequently, the first information layer 21 is formed on the optical separation layer 17. More specifically, first, the transmittance adjusting layer 209, the reflective layer 208, the second interface layer 205, the recording layer 204, the first interface layer 203 and the first dielectric layer 202 are formed in this order on the optical separation layer 17. It is also possible to form a second dielectric layer between the reflective layer 208 and the second interface layer 205. These layers can be formed by the method described in Embodiment 2.

Lastly, the transparent layer 13 is formed on the first dielectric layer 202. The transparent layer 13 can be formed by the method described in Embodiment 1.

It should be noted that it is also possible to perform an initialization step of crystallizing the entire recording layer 204, after the first dielectric layer 202 has been formed or after the transparent layer 13 has been formed. The crystallization of the recording layer 204 can be performed by irradiating a laser beam.

Moreover, it is possible to perform an initialization step of crystallizing the entire recording layer 304 of the second information layer 22 and the entire recording layer 204 of the first information layer 21 after forming the first dielectric layer 202 or after the transparent layer 13 has been formed. In this case, if the crystallization of the recording layer 204 of the first information layer 21 is performed first, then the laser power that is necessary for crystallizing the recording layer 304 of the second information layer 22 tends to become large, so that it is preferable to crystallize the recording layer 304 of the second information layer 22 first.

Thus, the information recording medium 20 can be manufactured as described above. It should be noted that in this embodiment, sputtering was used as the film forming method for each of the layers, but there is no limitation to this, and it is also possible to use such methods as vacuum vapor deposition, ion plating, CVD, or MBE or the like.

Embodiment 4

Figure 4:
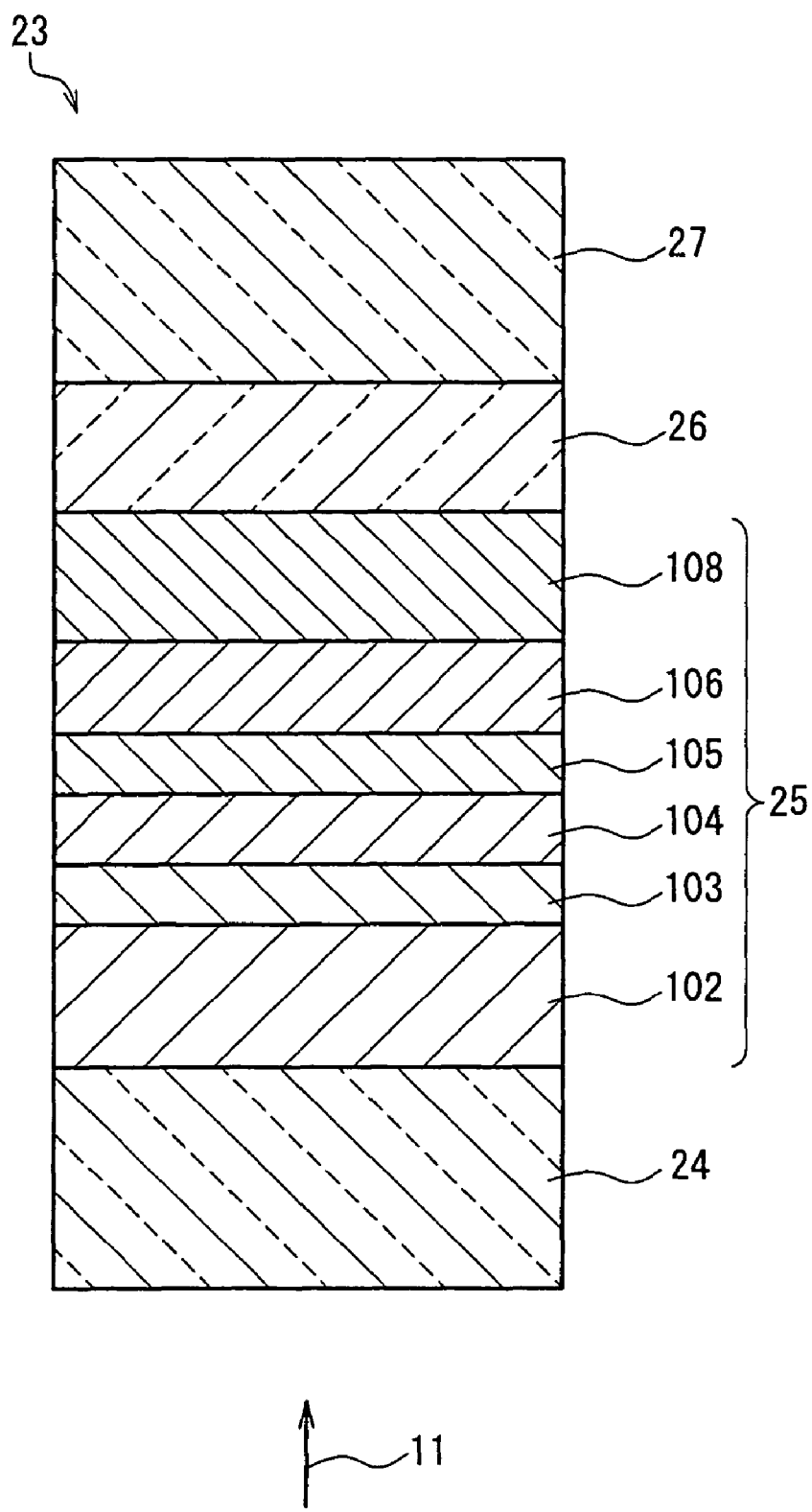
FIG. 4 is a partial cross-sectional view showing the configuration of an information recording medium according to Embodiment 4 of the present invention.

In Embodiment 4, another example of an information recording medium according to the present invention is explained. FIG. 4 shows a partial cross-sectional view of an information recording medium 23 according to Embodiment 4. Like the information recording medium 15 explained in Embodiment 1, the information recording medium 23 is an optical information recording medium with which information can be recorded and reproduced by irradiating a laser beam 11.

In the information recording medium 23, different to the information recording media 15, 19 and 20 explained in Embodiments 1 to 3, a substrate 24 is arranged on the side from which the laser beam is incident. The information recording medium 23 is formed by layering an information layer 25 on the substrate 24, and adhering a dummy substrate 27 on the information layer 25, with an adhesive layer 26 interposed between the information layer 25 and the dummy substrate 27.

The substrate 24 and the dummy substrate 27 are transparent and disk-shaped. For the substrate 24 and the dummy substrate 27, it is possible to use, for example, a resin such as polycarbonate, amorphous polyolefin or PMMA, or glass, as for the substrate 14 described in Embodiment 1.

It is also possible to form guide grooves for guiding the laser beam 11 in the surface of the substrate 24 on the side of the first dielectric layer 102. It is preferable that the surface of the substrate 24 that faces away from the first dielectric layer 102 and the surface of the dummy substrate 27 that faces away from the adhesive layer 26 are smooth. Polycarbonate is especially advantageous as the material for the substrate 24 and the dummy substrate 27, due to its excellent transfer properties and suitability for mass production, as well as its low cost. It is preferable that the thickness of the substrate 24 and the dummy substrate 27 is in the range of 0.3 mm to 0.9 mm, so that they are sufficiently strong, and the overall thickness of the information recording medium 23 becomes about 1.2 mm.

The adhesive layer 26 is made from a resin, such as a light-curing resin (in particular a UV-curing resin) or a delayed action type thermosetting resin. The adhesive layer 26 preferably has a small optical absorption with respect to the laser beam 11 that is used, and preferably has a small birefringence in the short wavelength region. It should be noted that it is preferable that the thickness of the adhesive layer 26 is in the range of 0.6 μm to 50 μm, due to the same reasons as for the optical separation layer 17.

The information layer 25 has the same film constitution as the information layer 16 described in Embodiment 1, and explanations for portions that are labeled by the same numerals as in Embodiment 1 have been omitted.

The information recording medium 23 can be manufactured by the method explained below.

First, the information layer 25 is formed on the substrate 24 (whose thickness is 0.6 mm, for example). If guide grooves for guiding the laser beam 11 are formed in the substrate 24, then the information layer 25 is formed on the side on which the guide grooves are formed. More specifically, the substrate 24 is placed in a film-forming device, and the first dielectric layer 102, the first interface layer 103, the recording layer 104, the second interface layer 105, the second dielectric layer 106 and the reflective layer 108 are layered in this order. It should be noted that a low thermal conductivity layer made of a material whose thermal conductivity is lower than that of the reflective layer 108 may be formed between the second dielectric layer 106 and the reflective layer 108. The method for forming the various layers is as explained in Embodiment 1.

Next, the substrate 24 on which the information layer 25 is layered and the dummy substrate 27 (whose thickness is 0.6 mm, for example) are glued together using an adhesive layer 26. More specifically, a light-curing resin (in particular a UV-curing resin) or a delayed action type thermosetting resin is applied on the dummy substrate 27, the substrate 24 on which the information layer 25 is layered is adhered to the dummy substrate 28 and spin-coating is performed, and then the resin is cured. Moreover, it is also possible to apply an adhesive resin uniformly to the dummy substrate 27 and adhere it to the substrate 24 on which the information layer 25 has been formed.

It should be noted that it is also possible to perform an initialization step of crystallizing the entire recording layer 104 after adhering the dummy substrate 27 to the substrate 24 on which the information layer 25 has been layered. The crystallization of the recording layer 104 can be performed by irradiating a laser beam.

Thus, the information recording medium 23 can be manufactured as described above. It should be noted that in this embodiment, sputtering was used as the film forming method for each of the layers, but there is no limitation to this, and it is also possible to use such methods as vacuum vapor deposition, ion plating, CVD, or MBE or the like.

The information recording medium 23 in which the substrate 24 is arranged on the side from which the laser beam is irradiated, as described above, has the same effects as the information recording media described in Embodiments 1 to 3.

Embodiment 5

Figure 5:
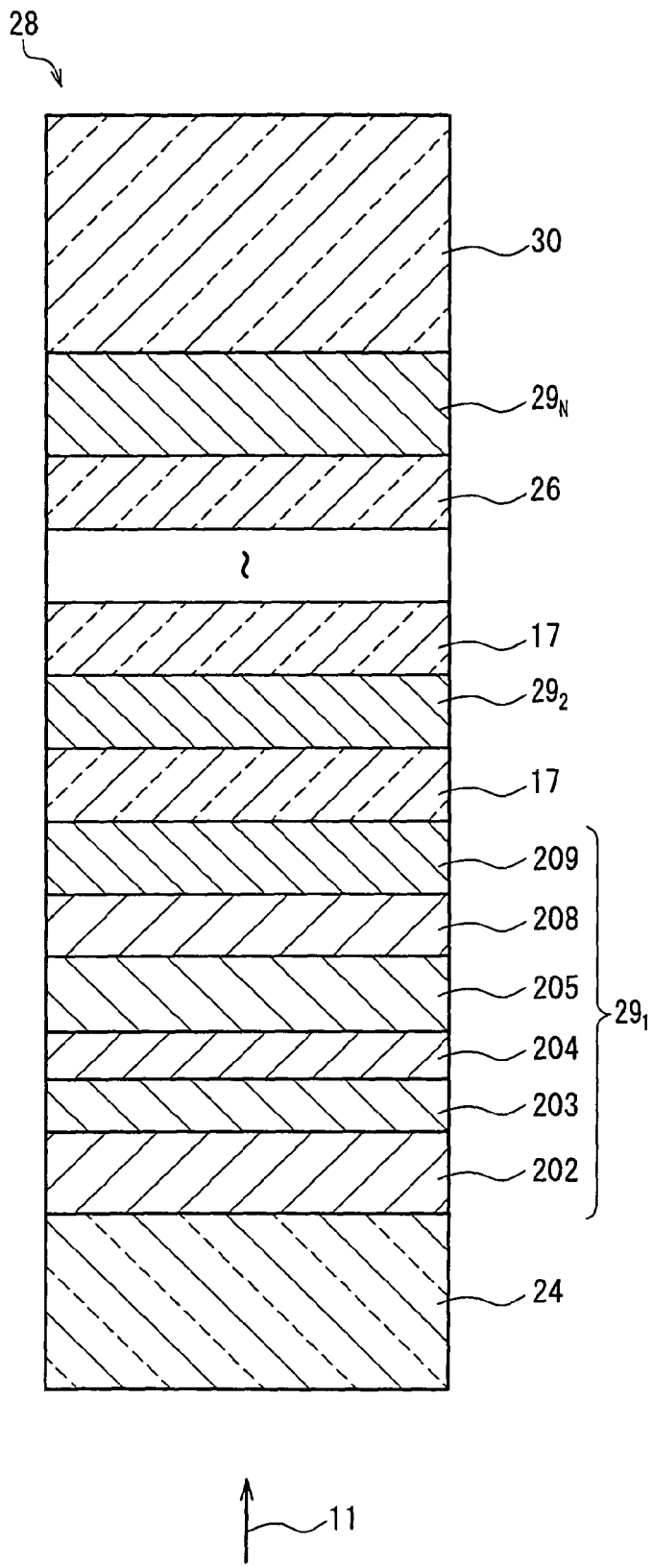
FIG. 5 is a partial cross-sectional view showing the configuration of an information recording medium according to Embodiment 5 of the present invention.

In Embodiment 5, another example of an information recording medium according to the present invention is explained. FIG. 5 shows a partial cross-sectional view of an information recording medium 28 according to Embodiment 5. Like the information recording medium 19 of Embodiment 2, the information recording medium 28 is a multi-layer optical information recording medium, which includes a plurality of information layers and with which information can be recorded and reproduced on the information layers by irradiating a laser beam 11 from one side.

The information recording medium 28 is made by adhering (N−1) information layers (first information layer $29_1$, second information layer $29_2$, ..., (N−1)th information layer $29_{N-1}$) layered in that order with optical separation layers 17 interposed in between on the substrate 24, to an information layer (N-th information layer $29_N$) formed on the substrate 30, with an adhesive layer 26.

The substrate 30 is transparent and disk-shaped. For the substrate 30, it is possible to use, for example, a resin such as polycarbonate, amorphous polyolefin or PMMA, or glass, as for the substrate 14 described in Embodiment 1.

It is also possible to form guide grooves for guiding the laser beam 11 in the surface of the substrate 30 on the side of the N-th information layer $29_N$. It is preferable that the surface of the substrate 30 on the side facing away from the N-th information layer $29_N$ is smooth. Polycarbonate is especially advantageous as the material for the substrate 30, due to its excellent transfer properties and suitability for mass production, as well as its low cost. It is preferable that the thickness of the substrate 30 is in the range of 0.3 mm to 0.9 mm, so that it is sufficiently strong, and the thickness of the information recording medium 23 becomes about 1.2 mm.

The first information layer $29_1$ has the same film configuration as the first information layer $18_1$ explained in Embodiment 2, so that further explanations thereof have been omitted. Also further explanations of the other portions labeled with the same numerals as in Embodiments 2 to 4 have been omitted.

The information recording medium 28 can be manufactured by the method explained below.

First, the first information layer $29_1$ is formed on the substrate 24 (whose thickness is 0.6 mm, for example). If guide grooves for guiding the laser beam 11 are formed in the substrate 24, then the first information layer $29_1$ is formed on the side on which the guide grooves are formed. More specifically, the substrate 24 is placed in a film-forming device, and the first dielectric layer 202, the first interface layer 203, the recording layer 204, the second interface layer 205, the reflective layer 208 and the transmittance adjusting layer 209 are layered in this order. It should be noted that it is also possible to form a further dielectric layer (second dielectric layer) between the second interface layer 205 and the reflective layer 208, if necessary. The method for forming the various layers is the same in Embodiment 2. After this, the second to (N−1)th information layer (i.e. (N−2) information layers) are layered in order, with optical separation layers interposed between them.

Moreover, the N-th information layer $29_N$ is formed on the substrate 30 (whose thickness is 0.6 mm, for example). As in the Embodiments 1 to 4, the information layers are made of single-layer films or multi-layer films, and the layers can be formed in a film-forming device by sputtering in order with a sputtering target of the corresponding material.

Finally, the substrate 24 and the substrate 30 on which the respective information layers have been layered are glued together with the adhesive layer 27. More specifically, a resin such as light-curing resin (in particular a UV-curing resin) or a delayed action type thermosetting resin may be applied on the N-th information layer, the substrate 24 on which the second to (N−1)th information layers are layered may be adhered to the N-th information layer and spin-coating may be performed, and then the resin may be cured. Moreover, it is also possible to apply an adhesive resin uniformly to the N-th information layer formed on the substrate 30 and adhere it to the (N−1)th information layer formed on the substrate 24.

It should be noted that after the substrate 24 and the substrate 30 have been joined together, it is possible to perform an initialization step of crystallizing the entire recording layer 204 included in the first information layer $29_1$. The crystallization of the recording layer 204 can be performed by irradiating a laser beam.

Thus, the information recording medium 28 can be manufactured as described above. It should be noted that in this embodiment, sputtering was used as the film forming method for each of the layers, but there is no limitation to this, and it is also possible to use such methods as vacuum vapor deposition, ion plating, CVD, or MBE or the like.

Embodiment 6

Figure 6:
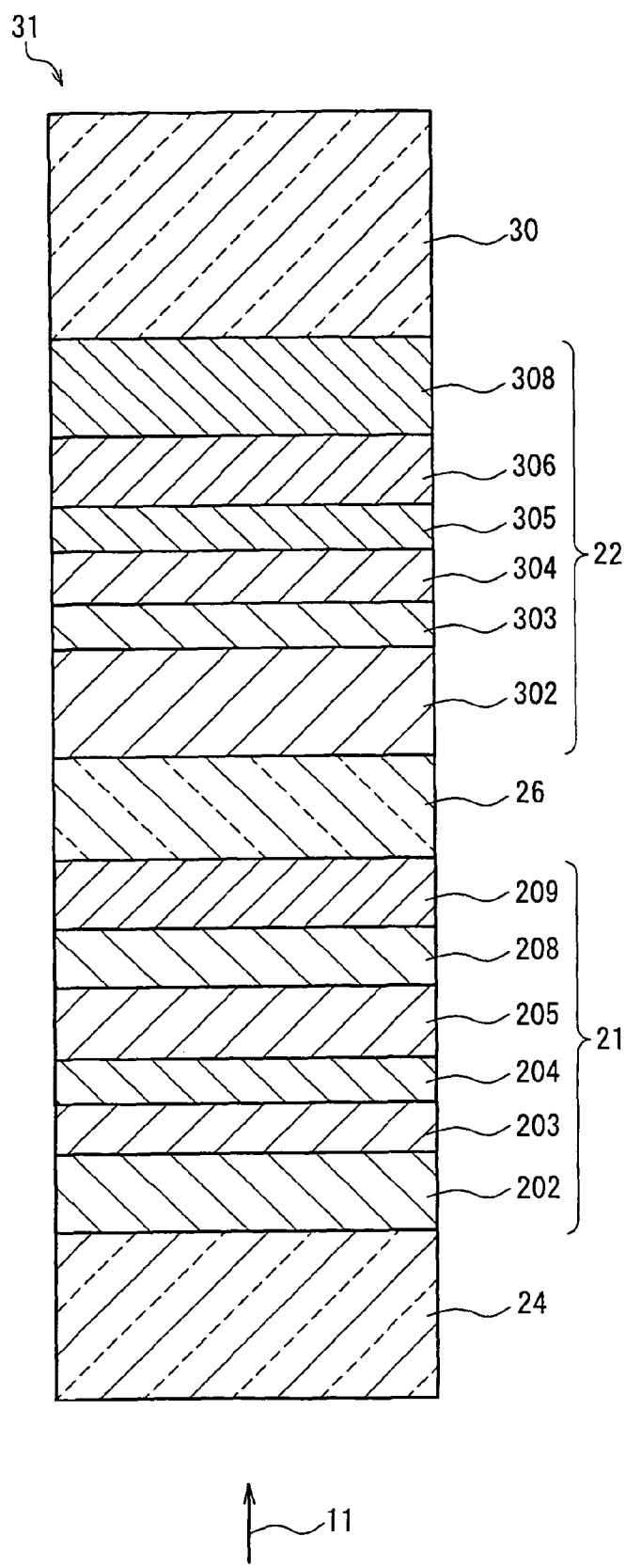
FIG. 6 is a partial cross-sectional view showing the configuration of an information recording medium according to Embodiment 6 of the present invention.

In Embodiment 6, an example of an information recording medium is explained, in which the multi-layer optical information recording medium in Embodiment 5 is provided with two information layers, that is, N=2. FIG. 6 shows a partial cross-sectional view of an information recording medium 31 according to Embodiment 6. Like the information recording medium 20 of Embodiment 3, the information recording medium 31 is a two-layer optical information recording medium, with which information can be recorded and reproduced on the information layers by irradiating a laser beam 11 from one side.

The information recording medium 31 includes a substrate 24 on which a first information layer 21 is formed, and a substrate 30 on which a second information layer 22 is formed, and is made by joining the first information layer 21 and the second information layer 22 together via an adhesive layer 26. It should be noted that the first information layer 21 and the second information layer 22 respectively have the same film configuration as the two information layers provided in the information recording medium explained in Embodiment 3, so that a further explanation of the various layers included in the first information layer 21 and the second information layer 22 has been omitted. Also the substrate 24, the substrate 30 and the adhesive layer 26 are as explained in Embodiments 4 and 5, so that their further explanation has been omitted.

The information recording medium 31 can be manufactured by the method explained below.

First, the first information layer 21 is formed on the substrate 24 (whose thickness is for example 0.6 mm) by the same method as explained in Embodiment 4.

If necessary, it is possible to perform an initialization step of crystallizing the entire recording layer 204 after the first dielectric layer 202 to the transmittance adjusting layer 209 have been formed. The crystallization of the recording layer 204 can be performed by irradiating a laser beam.

Moreover, the second information layer 22 is formed on the substrate 30 (whose thickness is 0.6 mm, for example). If guide grooves for guiding the laser beam 11 are formed in the substrate 30, then the second information layer 22 is formed on the side on which the guide grooves are formed. More specifically, the substrate 30 is placed in a film-forming device, and the reflective layer 308, the second dielectric layer 306, the second interface layer 305, the recording layer 304, the first interface layer 303, and the first dielectric layer 302 are layered in this order. It should be noted that a low thermal conductivity layer made of a material whose thermal conductivity is lower than that of the reflective layer 308 may be formed between the reflective layer 308 and the second dielectric layer 306. The method for forming the various layers is the same as the method explained in Embodiment 3.

It should be noted that it is also possible to perform an initialization step of crystallizing the entire recording layer 304 after the first dielectric layer 302 has been formed. The crystallization of the recording layer 304 can be performed by irradiating a laser beam.

Lastly, the substrate 24 on which the first information layer 21 has been formed and the substrate 30 on which the second information layer 22 has been formed are glued together using the adhesive layer 26. More specifically, a resin such as light-curing resin (in particular a UV-curing resin) or a delayed action type thermosetting resin may be applied on the first information layer 21 or the second information layer 22, the substrate 24 on which the first information layer 21 is formed may be adhered to the substrate 30 on which the second information layer 22 is formed and spin-coating may be performed, and then the resin may be cured. Moreover, it is also possible to apply an adhesive resin uniformly to the first information layer 21 or the second information layer 22 and adhere the substrate 24 provided with the first information layer 21 to the substrate 30 provided with the second information layer 22.

Moreover, if the recording layers 204 and 304 have not been initialized at the step of providing the first information layer 21 on the substrate 24 and the second information layer 22 on the substrate 30, then it is possible to perform an initializing step of crystallizing the entire recording layers 204 and 304 after the gluing step. In this case, it is preferable that the recording layer 304 included in the second information layer 22 is crystallized first, for the same reasons as described in Embodiment 3.

Thus, the information recording medium 31 can be manufactured as described above. It should be noted that in this embodiment, sputtering was used as the film forming method for each of the layers, but there is no limitation to this, and it is also possible to use such methods as vacuum vapor deposition, ion plating, CVD, or MBE or the like.

Embodiment 7

In Embodiment 7, an example of a method for recording and reproducing information with an optical information recording medium as explained in Embodiments 1 to 6 is described.

Figure 7:
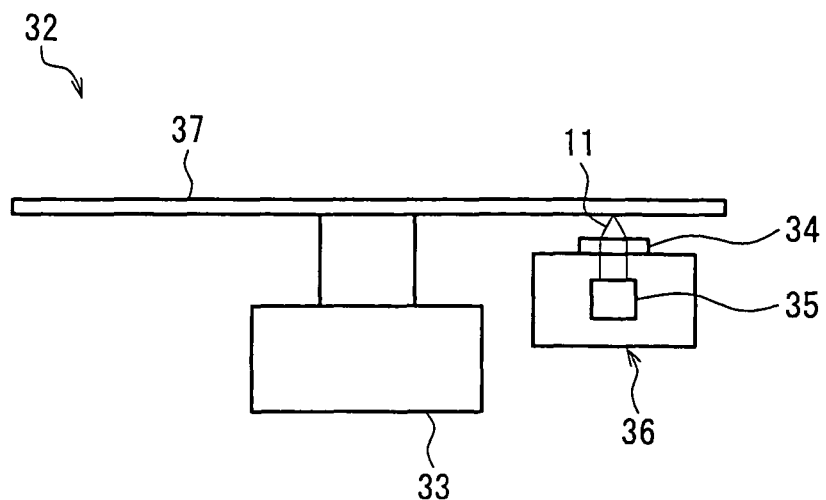
FIG. 7 is a schematic view showing the configuration of a portion of a recording/reproducing apparatus used recording and reproducing information on an information recording medium according to the present embodiment.

FIG. 7 diagrammatically shows the configuration of a portion of a recording/reproducing apparatus 32 used for an information recording/reproducing method according to the present embodiment. The recording/reproducing apparatus 32 includes a spindle motor 33 for rotating an information recording medium 37, and an optical head 36 provided with a semiconductor laser 35 and an objective lens 34 for focusing a laser beam 11 emitted from the semiconductor laser 35. The information recording medium 37 can be any of the information recording media explained in Embodiments 1 to 6, and is provided with a single information layer (for example the information layer 16 of the information recording medium 15 explained in Embodiment 1) or a plurality of information layers (for example the first information layer 21 and the second information layer 22 in the information recording medium 20 explained in Embodiment 3). The objective lens 34 focuses the laser beam 11 onto the information layer(s) of the information recording medium 37.

The recording, erasing and overwriting of information on the information recording medium is performed by modulating the power of the laser beam 11 between a peak power ($P_p$ (mW)) of high power and a bias power ($P_b$ (mW)) of low power. By irradiating a laser beam 11 with the peak power, an amorphous phase is formed in a local portion of the recording layer, and this amorphous phase serves as a recording mark. Between recording marks, a laser beam 11 of the bias power is irradiated, and a crystalline phase (erased portion) is formed. It should be noted that if the laser beam 11 is irradiated with the peak power, then so-called multi-pulses are common, in which a pulse train is formed. The multi-pulses may be formed by modulating only with the power levels of the peak power and the bias power, or they may be formed by modulating with power levels in the range of 0 . . . $P_p$ (mW).

Moreover, information signals are reproduced by setting as the reproduction power ($P_r$(mW)) a power that is lower than the power level of the peak power and the bias power, which does not influence the optical state of the recording marks when irradiating the laser beam 11 with this power level, and with which a sufficient amount of reflected light for the reproduction of the recording marks from the information recording medium can be attained. The signals from the information recording medium 37 obtained by irradiating a laser beam 11 with this reproduction power are read with a detector, thus reproducing the information signal.

The numerical aperture of the objective lens 34 is adjusted so that the spot diameter of the laser beam is within the range of 0.4 μm and 0.7 μm, preferably within the range of 0.5 and 1.1 μm (more preferably within the range of 0.6 and 0.9 μm). It is preferable that the wavelength of the laser beam is not greater than 450 nm (more preferably in the range of 350 nm to 450 nm). It is preferable that the linear speed of the information recording medium 37 when recording information is in the range of 1 m/sec to 20 m/sec (more preferably in the range of 2 m/sec to 15 m/sec), because in this range crystallization due to the reproduction light tends not to occur and a sufficient erasing capability is attained.

If, for example, the information recording medium 37 is the information recording medium 20 provided with two information layers (see FIG. 3), then when recording on the first information layer 21, the laser beam 11 is focused onto the recording layer 204 of the first information layer 21, and information is recorded on the recording layer 204 with the laser beam 11, which has passed through the transparent layer 13. The reproduction of information is performed using the laser beam 11 that has been reflected by the recording layer 204 and passed through the transparent layer 13. On the other hand, to record information on the second information layer 22, the laser beam 11 is focused on the recording layer 304 of the second information layer 22, and information is recorded with the laser beam 11, which has passed through the transparent layer 13, the first information layer 21 and the optical separation layer 17. The reproduction of information is performed using the laser beam 11 that has been reflected by the recording layer 304 and passed through the optical separation layer 17, the first information layer 21 and the transparent layer 13.

It should be noted that if guide grooves for guiding the laser beam 11 are formed in the surface of the substrate 14 and the optical separation layer 17 of the information recording medium 20, then the information may be recorded in the groove surfaces (grooves) that are closer to the side from which the laser beam 11 is irradiated, or in the groove surface (lands) that is further away therefrom. It is also possible to record information in both grooves and lands.

Embodiment 8

Figure 8:
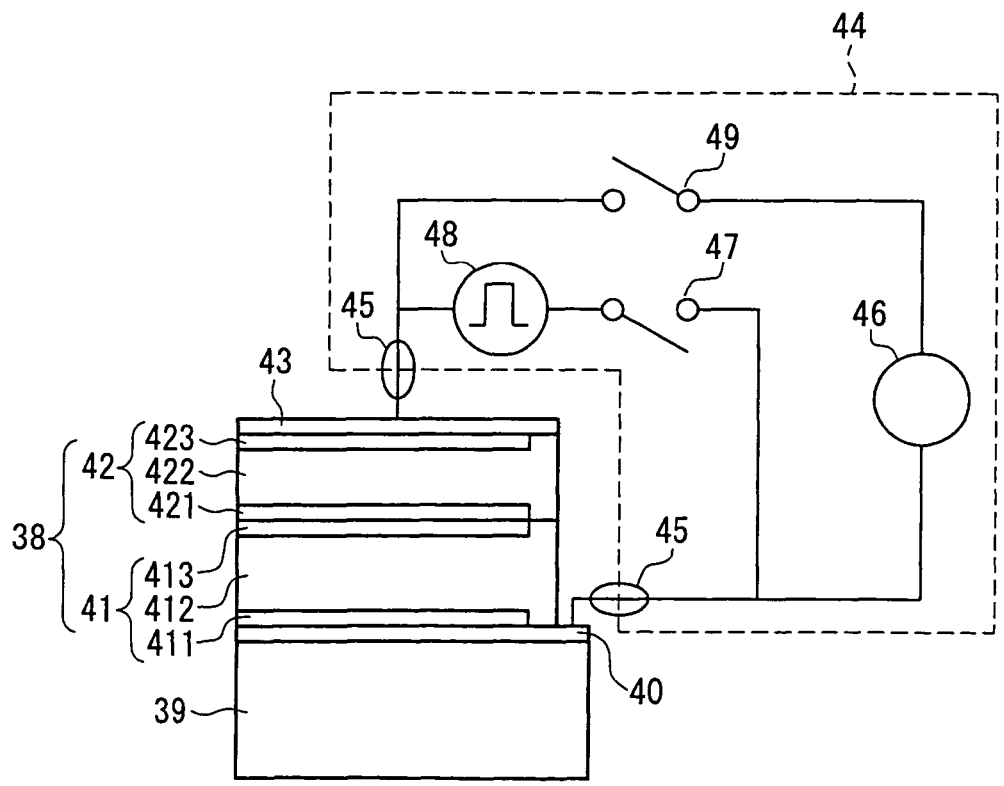
FIG. 8 is a schematic view showing a partial cross section of an information recording medium according to Embodiment 8 of the present invention, and an electric information recording/reproducing apparatus for recording and reproducing information on this information recording medium.

The following is an explanation of yet another embodiment of the information recording medium of the present invention. FIG. 8 is a diagram schematically showing a partial cross section of an information recording medium 38 and the schematic configuration of an electric information recording/reproducing apparatus according to the present embodiment. The information recording medium 38 according to the present embodiment is an electrical information recording medium with which information can be recorded and reproduced through the application of electrical energy (for example a current).

The information recording medium 38 of the present embodiment includes a substrate 39, and a lower electrode 40, a first information layer 41, a second information layer 42 and an upper electrode 43 layered in this order on the substrate 39. The first information layer 41 is made of a first interface layer 411, a recording layer 412 and a second interface layer 413 arranged in this order from the side of the substrate 39. The second information layer 42 is made of a first interface layer 421, a recording layer 422 and a second interface layer 423 arranged in this order from the side of the substrate 39.

For the material of the substrate 39, a resin such as polycarbonate, glass, a ceramic such as $Al_2O_3$, a semiconductor such as Si, or a metal such as Cu may be used. The following explanation is for the case that a Si substrate is used for the substrate 39.

The lower electrode 40 and the upper electrode 43 are provided for applying a current to the recording layer 412 of the first information layer 41 and the recording layer 422 of the second information layer 42.

The recording layers 412 and 422 are made of a material in which a reversible phase change between a crystalline phase and an amorphous phase can be induced by the Joule heat generated through the application of the current, and the recording of information utilizes the phenomenon that the specific resistance changes between the crystalline phase and the amorphous phase. For the material of the recording layers 412 and 413, the same materials as for the recording layers in the information recording media explained in Embodiments 1 to 6 can be used, and the recording layers 412 and 413 can be formed by the same method.

In the first information layer 41, the first interface layer 411 and the second interface layer 413 are provided in order to adjust the crystallization time of the recording layer 412. In the second information layer 42, the first interface layer 421 and the second interface layer 423 are provided in order to adjust the crystallization time of the recording layer 422.

For the material of the first interface layers 411 and 421 and the second interface layers 413 and 423, it is possible to use the same materials as for the first interface layer 103 and the second interface layer 105 in Embodiment 1, respectively.

For the lower electrode 40 and the upper electrode 43, it is possible to use a single metal, such as Al, Au, Ag, Cu, Pt or the like, or an alloy material having one or a plurality of these as its principal component, or an alloy material to which one or more other elements have been added in order to increase moisture resistance or to adjust the thermal conductivity. The lower electrode 40 and the upper electrode 43 can be formed in an Ar gas atmosphere by sputtering with a sputtering target of the metal material or the alloy material serving as the electrode material. It should be noted that it is also possible to form the layers by vacuum vapor deposition, ion-plating, CVD or MBE.

Figure 11:
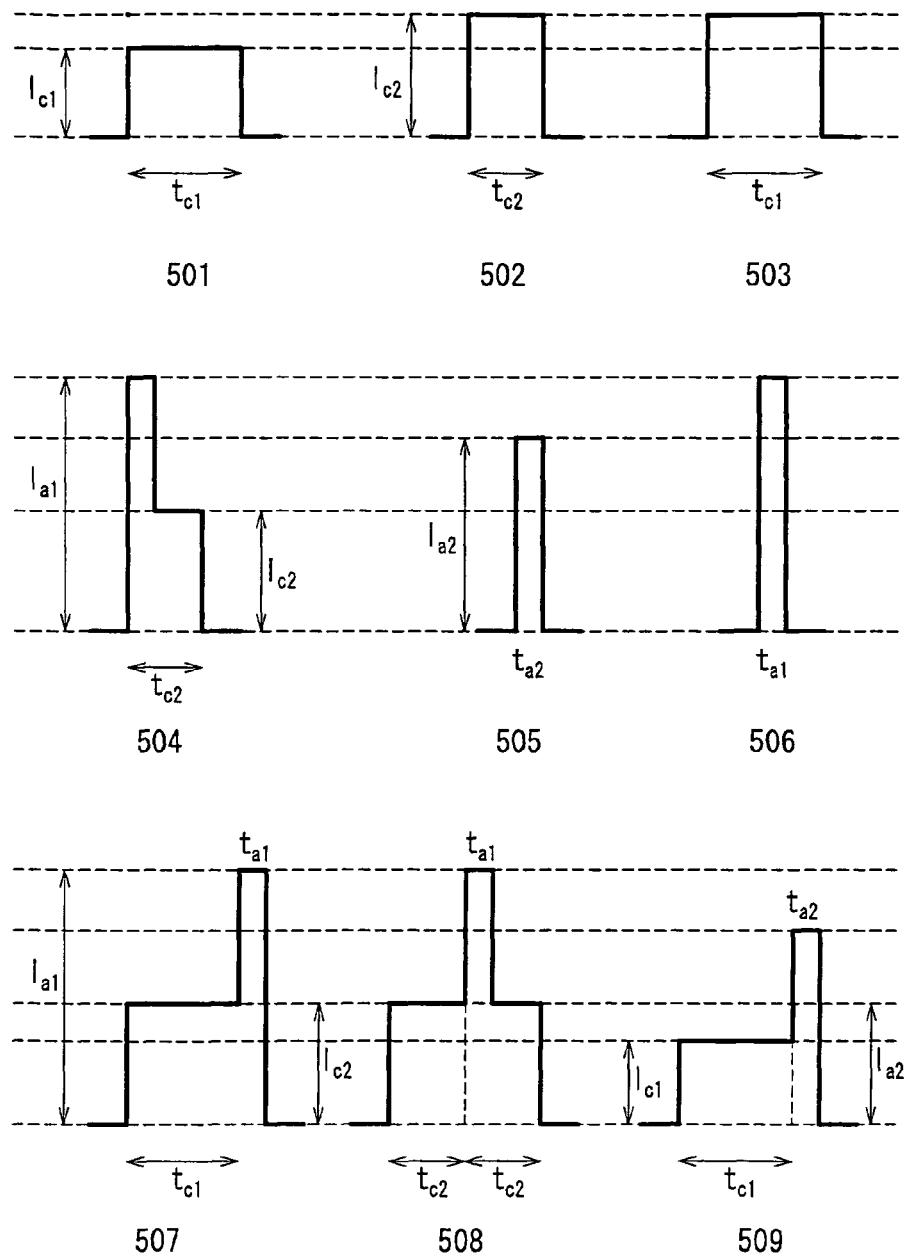
FIG. 11 is a view showing an example of recording and erasing pulses waveforms that are applied to an electric information recording/reproducing apparatus according to the present invention.
Figure 12:
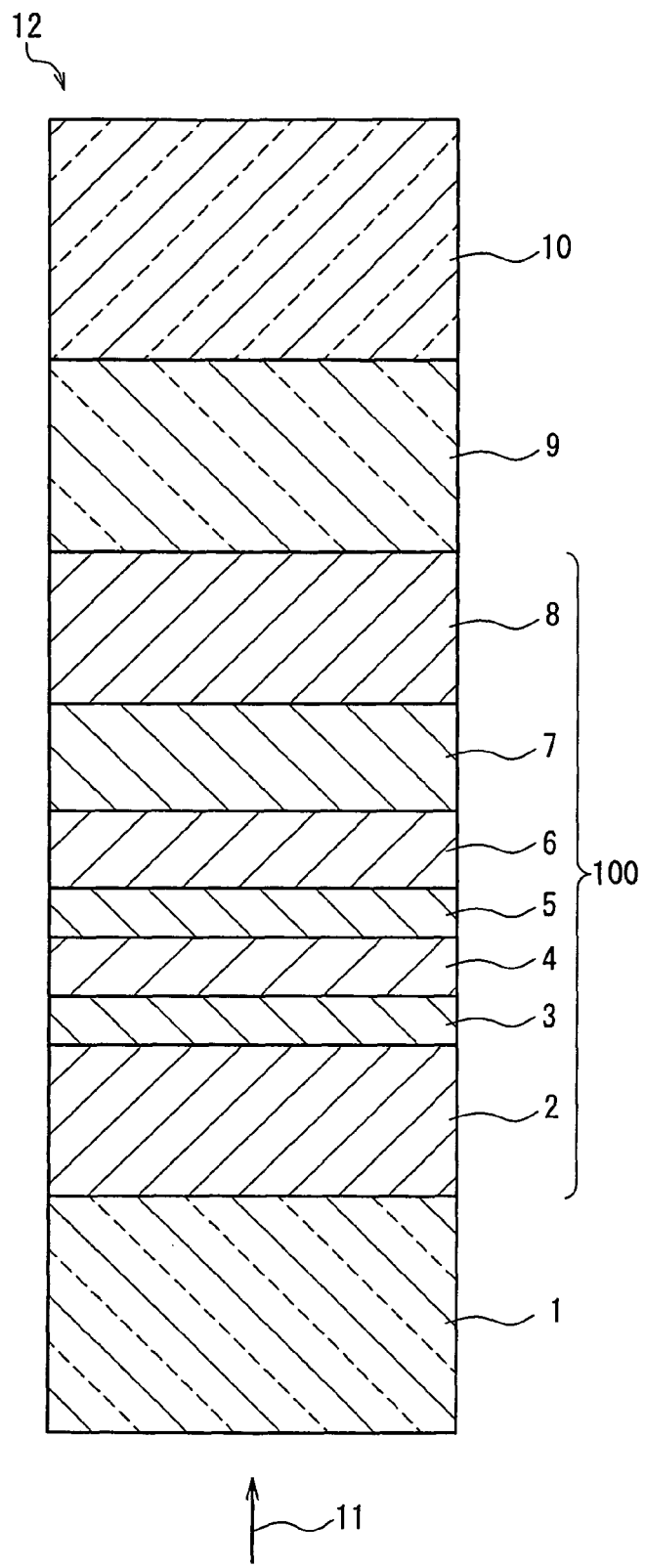
FIG. 12 is a partial cross-sectional view showing the configuration of a 4.7 GB DVD-RAM, which is an example of a conventional information recording medium.

The following is an explanation of the electrical information recording/reproducing apparatus 44 that is used for recording and reproducing information on the information recording medium 38. The electrical information recording/reproducing apparatus 44 according to this embodiment is electrically connected to the information recording medium 38 via application portions 45. This electrical information recording/reproducing apparatus 44 is provided with a pulse power source 48 for applying electrical pulses to the recording layers 412 and 422 that are arranged between the lower electrode 40 and the upper electrode 43 of the information recording medium 38. The pulse power source 48 is connected to a switch 47, and current pulses can be applied between the electrodes of the information recording medium 38 by closing this switch 47. The electrical information recording/reproducing apparatus 44 further is provided with a resistance measuring device 46 for detecting resistance changes due to phase changes in the recording layers 412 and 422. The resistance measuring device 46 is connected to a switch 49, and the resistance measuring device 46 can be connected to the information recording medium 38 by closing this switch 49. In order to change at least one of the recording layers 412 and 422 from the amorphous phase (high-resistance state) to the crystalline phase (low-resistance state), the switch 47 is closed (and the switch 49 is opened) to apply a current pulse between the electrodes, and the temperature of the portion to which the current pulse is applied, and the temperature of the portion to which the current is applied is kept, for the crystallization time, at a temperature that is higher than the crystallization temperature of the material and lower than its melting point. To change the recording layer back from the crystalline phase to the amorphous phase, a current pulse that is higher than during crystallization is applied for a short time, and the recording layer is set to a temperature that is higher than its melting point and melted, after which it is cooled rapidly. FIG. 11 shows an example of recording and erasing pulses waveforms that are output from the pulse current source 48 of the electric information recording/reproducing apparatus 44. These recording and erasing pulses waveforms are explained in more detail in the following working examples.

Let $r_{a1}$ be the resistance when the recording layer 412 of the first information layer 41 is in the amorphous phase, $r_{c1}$ be the resistance when the recording layer 412 is in the crystalline phase, $r_{a2}$ be the resistance when the recording layer 422 of the second information layer 42 is in the amorphous phase and $r_{c2}$ be the resistance when the recording layer 422 is in the crystalline phase. The sums of the resistances of the recording layer 412 and the recording layer 422 can be set to the four different values $r_{a1}+r_{a2}$, $r_{a1}+r_{c2}$, $r_{a2}+r_{c1}$ and $r_{c1}+r_{c2}$, if $r_{c1} \leq r_{c2} \leq r_{a1} < r_{a2}$ or $r_{c1} \leq r_{c2} \leq r_{a2} < r_{a1}$ or $r_{c2} \leq r_{c1} < r_{a1} < r_{a2}$ or $r_{c2} \leq r_{c1} < r_{a2} < r_{a1}$. Consequently, it is possible to detect four different states, that is two bits of information, by measuring the resistance between the electrodes with the resistance measuring device 46.

Figure 9:
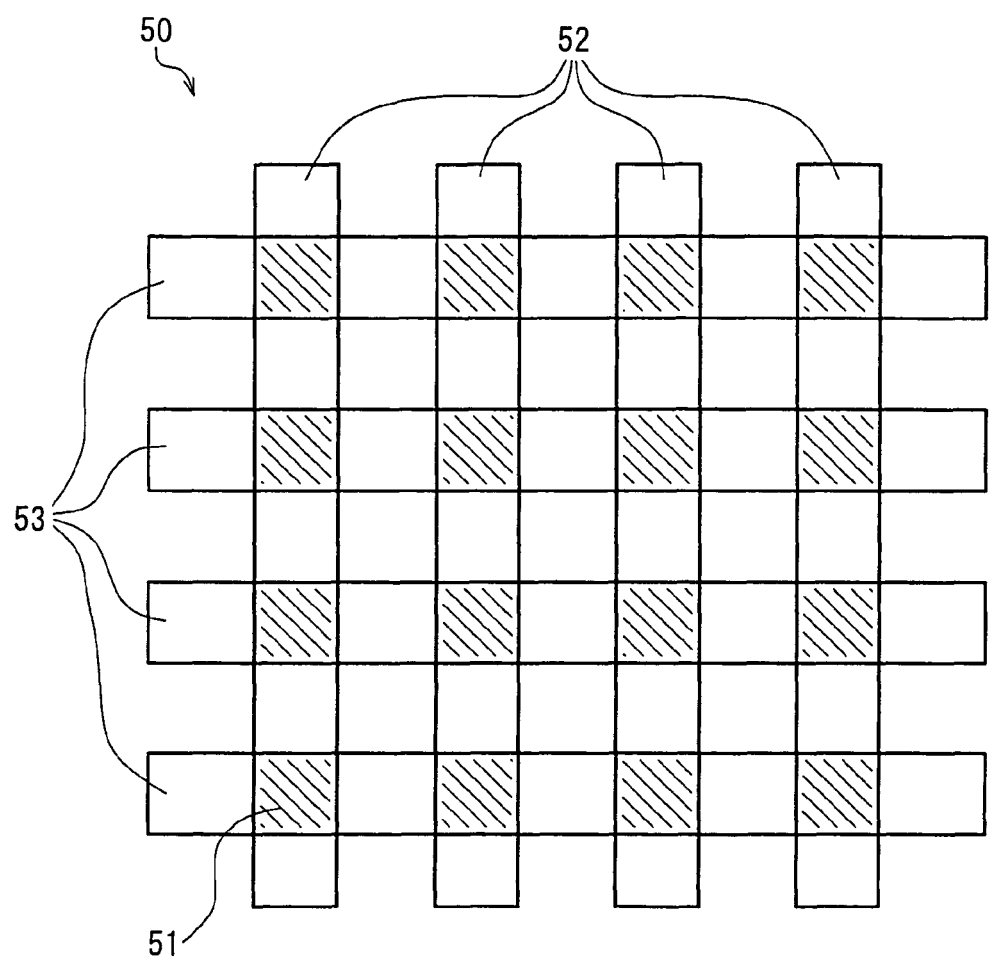
FIG. 9 is a schematic view showing a portion of the configuration of a large-capacity electric information recording medium according to Embodiment 8 of the present invention.

By arranging a multitude of these information recording media 38 in a matrix, it is possible to configure an electric information recording medium 50 with large capacity, as shown in FIG. 9. Each of the memory cells 51 of this electric information recording medium 50 is formed in a tiny region and with the same configuration as the information recording medium 38. The recording and reproducing of information in these memory cells 51 is performed by assigning one word line 52 and one bit line 53 to each of the memory cells 51.

Figure 10:
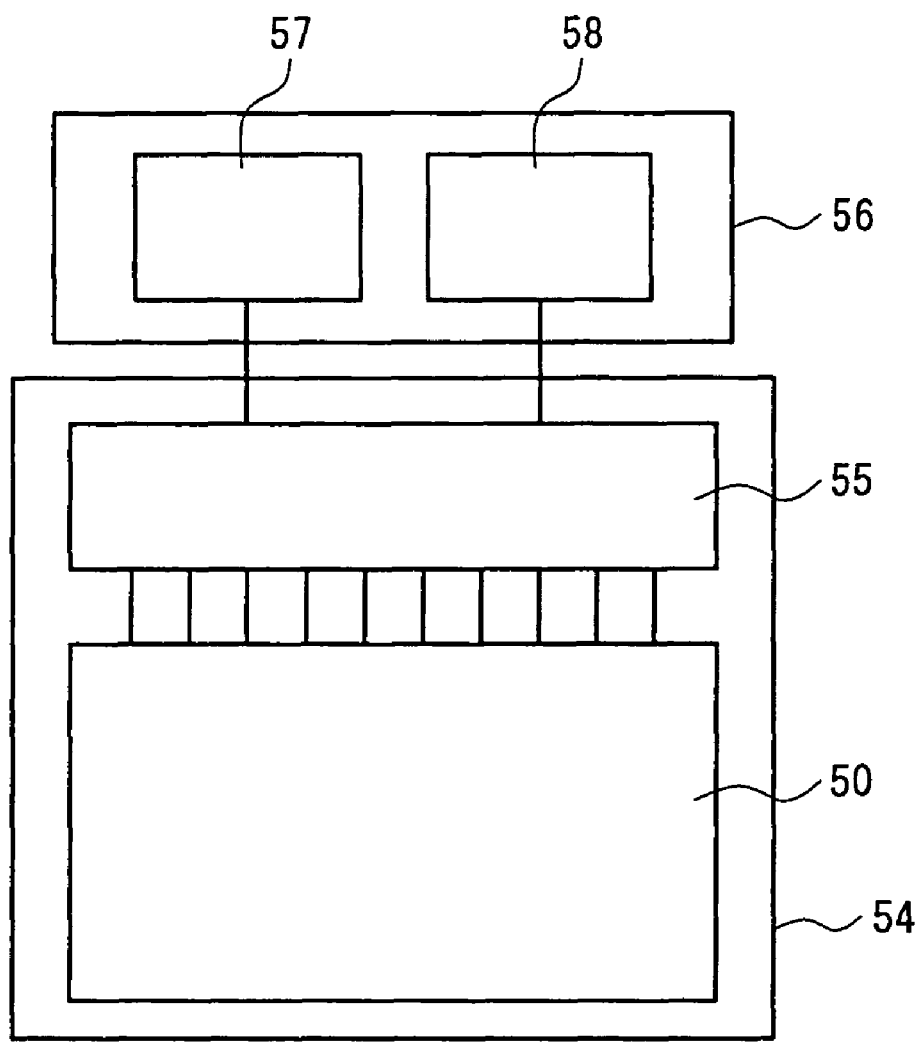
FIG. 10 is a schematic view showing a portion of the configuration of an electric information recording medium according to Embodiment 8 of the present invention and an information recording system using the same.

FIG. 10 shows a configuration example of an information recording system using the electric information recording medium 50. A storage device 54 includes the electric information recording medium 50 and an address specifying circuit 55. A word line 52 and a bit line 53 of the electric information recording medium 50 are specified by the address specifying circuit 55, and information can be recorded and reproduced with respect to each of the memory cells 51. Moreover, by electrically connecting the storage device 54 to an external circuit 56 including at least a pulse power source 57 and a resistance measuring device 58, it is possible to record and reproduce information in this electric information recording medium 50.

The information recording media of the foregoing Embodiments 1 to 9 were explained using examples in which (I) of the above-described materials (I) to (IV) was used as the material for the first interface layer and the second interface layer, but there is no limitation to this, and it is also possible to use any of the materials represented by (II) to (IV), thereby attaining the same effects.

WORKING EXAMPLES

The following is a more detailed explanation of the present invention using working examples.

Working Example 1

In Working Example 1, the information recording medium 15 in FIG. 1 was fabricated, and the relation between the materials of the first interface layer 103 and the second interface layer 105 to the recording sensitivity, signal strength and the repeated rewriting properties of the information layer 16 was determined. More specifically, a plurality of samples (1-1 to 1-5) with different materials for the first interface layer 103 and the second interface layer 105 were fabricated, and the recording sensitivity, the signal strength and the repeated rewriting properties of the information layer 16 were measured for each of these samples.

The samples were manufactured as follows. First, a polycarbonate substrate (diameter: 120 mm; thickness: 1.1 mm)

provided with guide grooves (depth: 20 nm; track pitch: 0.32 μm) for guiding the laser beam 11 was prepared as the substrate 14. Then, an Ag—Pd—Cu layer (thickness: 80 nm) serving as the reflective layer 108, a $(Bi_2O_3)_{80}(SiO_2)_{20}$ layer (thickness: 12 nm) serving as the second dielectric layer 106, a second interface layer 105 (thickness: 5 nm), a $Ge_{28}Sn_3Bi_2Te_{34}$ layer (thickness: 10 nm) serving as the recording layer 104, a first interface layer 103 (thickness: 5 nm), a $(ZnS)_{80}(SiO_2)_{20}$ layer (thickness: 60 nm) serving as the first dielectric layer 102 were formed in this order by sputtering on this polycarbonate substrate.

Lastly, a UV-curing resin was applied to the first dielectric layer 102, a polycarbonate sheet (diameter: 120 mm; thickness: 90 μm) was adhered to the first dielectric layer 102, and a uniform resin layer was formed by rotating the entire disk. After this, a transparent layer 13 of 100 μm thickness was formed by curing the UV-curing resin by irradiating UV light onto this resin layer. Thereafter, an initialization step of crystallizing was performed by irradiating a laser beam onto the recording layer 104. In this manner, a plurality of samples with different materials for the first interface layer 103 and the second interface layer 105 were manufactured.

Using the recording/reproducing apparatus 32 shown in FIG. 7, the recording sensitivity, signal strength and number of times of repeated rewriting of the information layer 16 in the information recording medium 15 was measured for the thus obtained samples. For this, the wavelength of the laser beam 11 was set to 405 nm, the numerical aperture of the objective lens 34 was set to 0.85, the linear speed of the samples during measurement was set to 4.9 m/s and 9.8 m/s, and the shortest mark length (2 T) was set to 0.149 μm. The information was recorded in grooves. The following is an explanation of the method for measuring the recording sensitivity, signal strength and number of times of repeated rewriting.

The recording sensitivity was evaluated by modulating the power of the laser beam 11 between 0 and $P_p$ (mW), recording random signals from a mark length of 0.149 μm (2 T) to 0.596 μm (8 T) with the (1-7) modulation method, and measuring, with a time interval analyzer, the front end jitter of the recording marks (jitter (discrepancy of the mark position) at the front end portion of the recording marks) and the rear end jitter of the recording marks (jitter (discrepancy of the mark position) at the rear end portion of the recording marks). It should be noted that the recording properties are better, the smaller the jitter. Moreover, $P_p$ and $P_b$ are set such that the average jitter (average value of the front end jitter and the rear end jitter) becomes minimal, and the optimum $P_p$ for this was taken as the recording sensitivity.

The signal strength was evaluated by modulating the power of the laser beam 11 between 0 and $P_p$ (mW), alternately recording signals with a mark length of 0.149 μm (2 T) and 0.671 μm (9 T) consecutively for 10 times in the same groove, and finally measuring with a spectrum analyzer the CNR (carrier-to-noise ratio) of the carrier level and the noise level at the frequency of the 2 T signal for overwriting with a 2 T signal. This CNR value was taken as the signal strength. It should be noted that the signal strength is stronger with larger CNR value.

The number of times of repeated rewriting was evaluated by modulating the power of the laser beam 11 between 0 and $P_p$ (mW) and consecutively recording random signals with mark lengths of 0.149 μm (2 T) to 0.596 μm (8 T) in the same grooves, and measuring the front end jitter and the rear end jitter at each of the recording rewriting cycles with a time interval analyzer. The number of rewriting cycles at which there was an increase of 3% with respect to the average jitter of the first time was taken as the upper limit of the number of times of repeated rewriting. It should be noted that $P_p$ and $P_b$ were determined such that the average jitter becomes minimal.

Tables 1 and 2 list the materials for the first interface layer 103 and the second interface layer 105 in the samples and the evaluation results regarding the recording sensitivity, signal strength and the repeated rewriting properties of the information layer 16. Table 1 shows the results for a linear speed of 4.9 m/s (1×) and Table 2 shows the results for a linear speed of 9.8 m/s (2×). In the tables, Zr—Ga—O means $(ZrO_2)_{50}(Ga_2O_3)_{50}$ and Zr—Cr—O means $(ZrO_2)_{50}(Cr_2O_3)_{50}$. In this table, Zr—Cr—O/Zr—Ga—O means that the interface layer is formed using a $(ZrO_2)_{50}(Cr_2O_3)_{50}$ layer and a $(ZrO_2)_{50}(Ga_2O_3)_{50}$ layer, and that the $(ZrO_2)_{50}(Cr_2O_3)_{50}$ layer is arranged on the side on which the recording layer is formed. For the recording sensitivity at 1× speed, a value of less than 5.2 mW was taken to be "good", a value of at least 5.2 mW and less than 6 mW was taken to be "fair" and a value of 6 mW or more was taken to be "poor." For the recording sensitivity at 2× speed, a value of less than 6 mW was taken to be "good", a value of at least 6 mW and less than 7 mW was taken to be "fair" and a value of 7 mW or more was taken to be "poor." For the signal strength at both 1× speed and 2× speed, a value of at least 48 dB was taken to be "good", a value of at least 45 dB and less than 48 dB was taken to be "fair" and a value of less than 45 dB was taken to be "poor." As for the repeated rewriting properties, at both 1× speed and 2× speed, a number of times of repeated rewriting of at least 1000 was taken to be "good", a number of at least 500 and less than 1000 was taken to be "fair" and a number of less than 500 was taken to be "poor."

TABLE 1 linear speed: 4.9 m/s

| sample No. | material of first interface layer 103 | material of second interface layer 105 | recording sensitivity | signal intensity | repeated rewriting properties |
|---|---|---|---|---|---|
| 1-1 | Ge—N | Ge—N | fair | fair | poor |
| 1-2 | Zr—Cr—O | Zr—Cr—O/ Zr—Ga—O | fair | good | good |
| 1-3 | Zr—Ga—O | Zr—Ga—O | good | good | good |
| 1-4 | Zr—Ga—O | Zr—Cr—O | good | good | good |
| 1-5 | Zr—Cr—O | Zr—Ga—O | good | good | good |

TABLE 2 linear speed: 9.8 m/s

| sample No. | material of first interface layer 103 | material of second interface layer 105 | recording sensitivity | signal intensity | repeated rewriting properties |
|---|---|---|---|---|---|
| 1-1 | Ge—N | Ge—N | fair | poor | fair |
| 1-2 | Zr—Cr—O | Zr—Cr—O/ Zr—Ga—O | fair | good | good |
| 1-3 | Zr—Ga—O | Zr—Ga—O | good | fair | fair |
| 1-4 | Zr—Ga—O | Zr—Cr—O | good | fair | good |
| 1-5 | Zr—Cr—O | Zr—Ga—O | good | good | good |

As a result, it was found that in the sample 1-1 using Ge—N for the first interface layer 103 and the second interface layer 105 (comparative example), the repeated rewriting properties at 1× speed are insufficient. Moreover, it was found that in the samples 1-2, 1-3, 1-4 and 1-5 using the above-noted compositions (I) to (IV) for the first interface layer 103 and the second interface layer 105, the recording sensitivity, the signal strength and the repeated rewriting properties are good. It was found that in particular in the sample 1-5, in which $(ZrO_2)_{50}(Cr_2O_3)_{50}$ is used for the first interface layer 103 and $(ZrO_2)_{50}(Ga_2O_3)_{50}$ is used for the second interface layer 105, the recording sensitivity, the signal strength and the repeated rewriting properties are all particularly good.

Additional Examples

Working Example 2

In Working Example 2, information recording media 15 as shown in FIG. 1 was fabricated, and the relation between the material of the second interface layer 105 and the repeated rewriting properties of the information layer 16 was examined. More specifically, a plurality of samples (2-1 to 2-17) with different materials for the second interface layer 105 were fabricated, and the number of times of repeated rewriting of the information layer 16 was measured for each of these samples.

The samples were manufactured as follows. First, a polycarbonate substrate (diameter: 120 mm; thickness: 1.1 mm) provided with guide grooves (depth: 20 nm; track pitch: 0.32 µm) for guiding the laser beam 11 was prepared as the substrate 14. Then, an Ag—Pd—Cu layer (thickness: 80 nm) serving as the reflective layer 108, a $(Bi_2O_3)_{50}(SiO_2)_{20}$ layer (thickness: 12 nm) serving as the second dielectric layer 106, a second interface layer 105 (thickness: 5 nm), a $Ge_{28}Sn_3Bi_2Te_{34}$ layer (thickness: 10 nm) serving as the recording layer 104, a $(ZrO_2)_{50}(Ga_2O_3)_{50}$ layer (thickness: 5 nm) serving as the first interface layer 103, a $(ZnS)_{80}(SiO_2)_{20}$ layer (thickness: 60 nm) serving as the first dielectric layer 102 were formed in this order by sputtering on this polycarbonate substrate.

Lastly, a UV-curing resin was applied to the first dielectric layer 102, a polycarbonate sheet (diameter: 120 mm; thickness: 90 µm) was adhered to the first dielectric layer 102, and a uniform resin layer was formed by rotating the entire disk. Next, the UV-curing resin was cured by irradiating UV light on this resin layer. Thus, a transparent layer 13 of 100 µm thickness was formed.

Thereafter, an initialization step of crystallizing the recording layer 104 was performed by irradiating a laser beam onto the recording layer 104. In this manner, a plurality of samples were manufactured in which the first interface layer 103 and the second interface layer 105 provided on both sides of the recording layer 104 are Ga-containing layers, and in which different materials are used for the second interface layer 105.

The repeated rewriting properties of the information recording media 15 of the resulting samples were evaluated using the recording/reproducing apparatus 32 shown in FIG. 7. For this, the wavelength of the laser beam 11 was set to 405 nm, the numerical aperture of the objective lens 34 was set to 0.85, the linear speed of the samples during measurement was set to 4.9 m/s and 9.8 m/s, and the shortest mark length (2 T) was set to 0.149 µm. The information was recorded in grooves. The method for measuring the number of times of repeated rewriting is the same as in Working Example 1.

Tables 3 and 4 list the materials for the second interface layer 105 of the information layer 16 in the information recording media 15 and the evaluation results regarding the repeated rewriting properties of the information layer 16. Table 3 shows the results for a linear speed of 4.9 m/s (1×) and Table 4 shows the results for a linear speed of 9.8 m/s (2×). As for the evaluation of the repeated rewriting properties, a number of times of repeated rewriting of at least 10000 was taken to be "very good", a number of at least 1000 and less than 10000 was taken to be "good".

TABLE 3

| sample No. | material of second interface layer 105 (mol %) | linear speed: 4.9 m/s number of times of repeated rewriting |
|---|---|---|
| 2-1 | $(Ga_2O_3)_5(ZrO_2)_{95}$ | good |
| 2-2 | $(Ga_2O_3)_{10}(ZrO_2)_{90}$ | very good |
| 2-3 | $(Ga_2O_3)_{50}(ZrO_2)_{50}$ | very good |
| 2-4 | $(Ga_2O_3)_{90}(ZrO_2)_{10}$ | very good |
| 2-5 | $(Ga_2O_3)_{95}(ZrO_2)_5$ | good |
| 2-6 | $(Ga_2O_3)_{10}(HfO_2)_{90}$ | very good |
| 2-7 | $(Ga_2O_3)_{50}(HfO_2)_{50}$ | very good |
| 2-8 | $(Ga_2O_3)_{90}(HfO_2)_{10}$ | very good |
| 2-9 | $(Ga_2O_3)_{10}(ZrO_2)_{45}(SiO_2)_{45}$ | very good |
| 2-10 | $(Ga_2O_3)_{50}(ZrO_2)_{25}(SiO_2)_{25}$ | very good |
| 2-11 | $(Ga_2O_3)_{90}(ZrO_2)_5(SiO_2)_5$ | very good |
| 2-12 | $(Ga_2O_3)_{10}(ZrO_2)_{85}(Y_2O_3)_5$ | very good |
| 2-13 | $(Ga_2O_3)_{50}(ZrO_2)_{45}(Y_2O_3)_5$ | very good |
| 2-14 | $(Ga_2O_3)_{90}(ZrO_2)_8(Y_2O_3)_2$ | very good |
| 2-15 | $(Ga_2O_3)_{10}(ZrO_2)_{40}(Y_2O_3)_5(SiO_2)_{45}$ | very good |
| 2-16 | $(Ga_2O_3)_{50}(ZrO_2)_{20}(Y_2O_3)_5(SiO_2)_{25}$ | very good |
| 2-17 | $(Ga_2O_3)_{90}(ZrO_2)_3(Y_2O_3)_2(SiO_2)_5$ | very good |

TABLE 4

| sample No. | material of second interface layer 105 (mol %) | linear speed: 9.8 m/s number of times of repeated rewriting |
|---|---|---|
| 2-1 | $(Ga_2O_3)_5(ZrO_2)_{95}$ | very good |
| 2-2 | $(Ga_2O_3)_{10}(ZrO_2)_{90}$ | very good |
| 2-3 | $(Ga_2O_3)_{50}(ZrO_2)_{50}$ | very good |
| 2-4 | $(Ga_2O_3)_{90}(ZrO_2)_{10}$ | very good |
| 2-5 | $(Ga_2O_3)_{95}(ZrO_2)_5$ | good |
| 2-6 | $(Ga_2O_3)_{10}(HfO_2)_{90}$ | very good |
| 2-7 | $(Ga_2O_3)_{50}(HfO_2)_{50}$ | very good |
| 2-8 | $(Ga_2O_3)_{90}(HfO_2)_{10}$ | very good |
| 2-9 | $(Ga_2O_3)_{10}(ZrO_2)_{45}(SiO_2)_{45}$ | very good |
| 2-10 | $(Ga_2O_3)_{50}(ZrO_2)_{25}(SiO_2)_{25}$ | very good |
| 2-11 | $(Ga_2O_3)_{90}(ZrO_2)_5(SiO_2)_5$ | very good |
| 2-12 | $(Ga_2O_3)_{10}(ZrO_2)_{85}(Y_2O_3)_5$ | very good |
| 2-13 | $(Ga_2O_3)_{50}(ZrO_2)_{45}(Y_2O_3)_5$ | very good |
| 2-14 | $(Ga_2O_3)_{90}(ZrO_2)_8(Y_2O_3)_2$ | very good |
| 2-15 | $(Ga_2O_3)_{10}(ZrO_2)_{40}(Y_2O_3)_5(SiO_2)_{45}$ | very good |
| 2-16 | $(Ga_2O_3)_{50}(ZrO_2)_{20}(Y_2O_3)_5(SiO_2)_{25}$ | very good |
| 2-17 | $(Ga_2O_3)_{90}(ZrO_2)_3(Y_2O_3)_2(SiO_2)_5$ | very good |

As a result, it could be confirmed that when a material represented by the composition formula $(Ga_2O_3)_{C1}(Z1)_{100-C1}$ is used for the second interface layer 105, then the repeated rewriting properties are particularly good in the samples in which C1 is in the range of $10 \leq C1 \leq 90$ (samples 2-2 to 2-4 and 2-6 to 2-17).

Working Example 3

In Working Example 3, information recording media 20 as shown in FIG. 3 were fabricated, and the relation between the material of the first interface layer 303 and the second interface layer 305 to the recording sensitivity, signal strength and repeated rewriting properties of the second information layer 22 was examined. More specifically, a plurality of samples (3-1 to 3-5) with different materials for the first interface layer 303 and the second interface layer 305 were fabricated, and the recording sensitivity, signal strength and number of times of repeated rewriting of the second information layer 22 were measured.

The samples were manufactured as follows. First, a polycarbonate substrate (diameter: 120 mm; thickness: 1.1 mm) provided with guide grooves (depth: 20 nm; track pitch: 0.32

μm) for guiding the laser beam 11 was prepared as the substrate 14. Then, an Ag—Pd—Cu layer (thickness: 80 nm) serving as the reflective layer 208, a $(Bi_2O_3)_{80}(SiO_2)_{20}$ layer (thickness: 12 nm) serving as the second dielectric layer 306, a second interface layer 305 (thickness: 5 nm), a $Ge_{28}Sn_3Bi_2Te_{34}$ layer (thickness: 10 nm) serving as the recording layer 304, a first interface layer 303 (thickness: 5 nm), and a $(ZnS)_{80}(SiO_2)_{20}$ layer (thickness: 60 nm) serving as the first dielectric layer 302 were formed in this order by sputtering on this polycarbonate substrate.

Next, a UV-curing resin was applied on the first dielectric layer 302, a transfer substrate provided with grooves (depth: 20 nm; track pitch: 0.32 μm) was adhered thereon, and a uniform resin layer was formed by rotating the entire disk, and after curing the UV-resin by irradiation of UV light on this resin layer, the transfer substrate was stripped off. Through this step, a 25 μm thick optical separation layer 17 provided with guide grooves for guiding the laser beam 11 was formed on the side of the first information layer 21.

After this, a $TiO_2$ layer (thickness: 20 nm) serving as the transmittance adjusting layer 209, an Ag—Pd—Cu layer (thickness: 10 nm) serving as the reflective layer 208, a $(ZrO_2)_{25}(SiO_2)_{25}(Ga_2O_3)_{50}$ layer (thickness: 10 nm) serving as the second interface layer 205, a $Ge_{28}Sn_3Bi_2Te_{34}$ layer (thickness: 6 nm) serving as the recording layer 204, a $(ZrO_2)_{25}(SiO_2)_{25}(Cr_2O_3)_{50}$ layer (thickness: 5 nm) serving as the first interface layer 203, and a $(ZnS)_{80}(SiO_2)_{20}$ layer (thickness: 40 nm) serving as the first dielectric layer 202 were formed in this order by sputtering on the optical separation layer 17.

Lastly, a UV-curing resin was applied to the first dielectric layer 202, a polycarbonate sheet (diameter: 120 mm; thickness: 65 μm) was adhered to the first dielectric layer 202, and a uniform resin layer was formed by rotating the entire disk. Next, the UV-curing resin was cured by irradiating UV light on this resin layer, thus forming a 75 μm thick transparent layer 13. After this, an initialization step of crystallizing the recording layer 304 of the second information layer 22 and the recording layer 204 of the first information layer 21 was performed by irradiation of a laser beam. In this manner, a plurality of samples with different materials for the first interface layer 303 and the second interface layer 305 were manufactured.

The recording sensitivity, signal strength and number of times of repeated rewriting of the second information layer 23 of the information recording media 20 of the resulting samples were evaluated using the recording/reproducing apparatus 32 shown in FIG. 7. For this, the wavelength of the laser beam 11 was set to 405 nm, the numerical aperture of the objective lens 34 was set to 0.85, the linear speed of the samples during measurement was set to 4.9 m/s and 9.8 m/s, and the shortest mark length (2 T) was set to 0.149 μm. The information was recorded in grooves. The methods for measuring the recording sensitivity, the signal strength and the number of times of repeated rewriting are the same as in Working Example 1.

Tables 5 and 6 list the materials for the first interface layer 303 and the second interface layer 305 of the second information layer 22 of the information recording media 20 and the evaluation results regarding the recording sensitivity, signal strength and the repeated rewriting properties of the second information layer 22. Table 5 shows the results for a linear speed of 4.9 m/s (1×) and Table 6 shows the results for a linear speed of 9.8 m/s (2×). In the tables, Zr—Ga—O means $(ZrO_2)_{50}(Ga_2O_3)_{50}$ and Zr—Cr—O means $(ZrO_2)_{50}(Cr_2O_3)_{50}$. In this table, Zr—Cr—O/Zr—Ga—O means that the interface layer is formed using a $(ZrO_2)_{50}(Cr_2O_3)_{50}$ layer and a $(ZrO_2)_{50}(Ga_2O_3)_{50}$ layer, and that the $(ZrO_2)_{50}(Cr_2O_3)_{50}$ layer is arranged the side on which the recording layer is formed. For the recording sensitivity at 1× speed, a value of less than 10.4 mW was taken to be "good", a value of at least 10.4 mW and less than 12 mW was taken to be "fair" and a value of 12 mW or more was taken to be "poor." For the recording sensitivity at 2× speed, a value of less than 12 mW was taken to be "good", a value of at least 12 mW and less than 14 mW was taken to be "fair" and a value of 14 mW or more was taken to be "poor." For the signal strength at both 1× speed and 2× speed, a value of at least 44 dB was taken to be "good", a value of at least 41 dB and less than 44 dB was taken to be "fair" and a value of less than 41 dB was taken to be "poor." As for the repeated rewriting properties, at both 1× speed and 2× speed, a number of times of repeated rewriting of at least 1000 was taken to be "good", a number of at least 500 and less than 1000 was taken to be "fair" and a number of less than 500 was taken to be "poor."

TABLE 5

| | | | linear speed: 4.9 m/s | | |
|---|---|---|---|---|---|
| sample No. | material of first interface layer 303 | material of second interface layer 305 | recording sensitivity | signal intensity | repeated rewriting properties |
| 3-1 | Ge—N | Ge—N | fair | fair | poor |
| 3-2 | Zr—Cr—O | Zr—Cr—O/ Zr—Ga—O | fair | good | good |
| 3-3 | Zr—Ga—O | Zr—Ga—O | good | good | good |
| 3-4 | Zr—Ga—O | Zr—Cr—O | good | good | good |
| 3-5 | Zr—Cr—O | Zr—Ga—O | good | good | good |

TABLE 6

| | | | linear speed: 9.8 m/s | | |
|---|---|---|---|---|---|
| sample No. | material of first interface layer 303 | material of second interface layer 305 | recording sensitivity | signal intensity | repeated rewriting properties |
| 3-1 | Ge—N | Ge—N | fair | poor | fair |
| 3-2 | Zr—Cr—O | Zr—Cr—O/ Zr—Ga—O | fair | good | good |
| 3-3 | Zr—Ga—O | Zr—Ga—O | good | fair | fair |
| 3-4 | Zr—Ga—O | Zr—Cr—O | good | fair | good |
| 3-5 | Zr—Cr—O | Zr—Ga—O | good | good | good |

As a result, it was found that in the sample 3-1 using Ge—N for the first interface layer 303 and the second interface layer 305 (comparative example), the repeated rewriting properties at 1× speed are insufficient. Moreover, it was found that in the samples 3-2, 3-3, 3-4 and 3-5 using the above-noted compositions (I) to (IV) for the first interface layer 303 and the second interface layer 305, the recording sensitivity, the signal strength and the repeated rewriting properties are good. It was found that in particular in the sample 3-5, in which $(ZrO_2)_{50}(Cr_2O_3)_{50}$ is used for the first interface layer 303 and $(ZrO_2)_{50}(Ga_2O_3)_{50}$ is used for the second interface layer 305, the recording sensitivity, the signal strength and the repeated rewriting properties are all particularly good.

Additional Examples

Working Example 4

In Working Example 4, information recording media 20 as shown in FIG. 3 were fabricated, and the relation between the material of the second interface layer 305 of the second information layer 22 to the repeated rewriting properties of the second information layer 22 was examined. More specifically, samples of information recording media 20 including second information layer 22 with different materials for the second interface layer 305 were fabricated, and the number of times of repeated rewriting of the second information layer 22 was measured for each of these samples. It should be noted that the samples of this working example were fabricated in the same manner as the samples of Working Example 3, except that $(ZrO_2)_{50}(Ga_2O_3)_{50}$ was used for the first interface layer 303 and the materials listed in Table 3 used in Working Example 2 were used for the second interface layer 305.

As a result to evaluating the repeated rewriting properties in the same manner as in Working Example 2, it could be confirmed that when a material represented by the composition formula $(Ga_2O_3)_{C1}(Z1)_{100-C1}$ is used for the second interface layer 305, then the repeated rewriting properties are particularly good in the samples in which C1 is in the range of $10 \leq C1 \leq 90$, which is similar to the result obtained in Working Example 2.

Working Example 5

In Working Example 5, information recording media 20 as shown in FIG. 3 were fabricated, and the relation between the material of the first interface layer 203 and the second interface layer 205 in the first information layer 21 to the recording sensitivity, signal strength and repeated rewriting properties of the first information layer 21 was examined. More specifically, a plurality of samples (5-1 to 5-5) with different materials for the first interface layer 203 and the second interface layer 205 were fabricated, and the recording sensitivity, signal strength and number of times of repeated rewriting of the first information layer 21 were measured.

The samples were manufactured as follows. First, a polycarbonate substrate (diameter: 120 mm; thickness: 1.1 mm) provided with guide grooves (depth: 20 nm; track pitch: 0.32 μm) for guiding the laser beam 11 was prepared as the substrate 14. Then, an Ag—Pd—Cu layer (thickness: 80 nm) serving as the reflective layer 308, a $(Bi_2O_3)_{80}(SiO_2)_{20}$ layer (thickness: 12 nm) serving as the second dielectric layer 306, a $(ZrO_2)_{25}(SiO_2)_{25}(Ga_2O_3)_{50}$ layer (thickness: 5 nm) serving as the second interface layer 305, a $Ge_{28}Sn_3Bi_3Te_{34}$ layer (thickness: 10 nm) serving as the recording layer 304, a $(ZrO_2)_{25}(SiO_2)_{25}(Cr_2O_3)_{50}$ layer (thickness: 5 nm) serving as the first interface layer 303, a $(ZnS)_{80}(SiO_2)_{20}$ layer (thickness: 60 nm) serving as the first dielectric layer 302 were formed in this order by sputtering on this polycarbonate substrate.

Next, a UV-curing resin was applied on the first dielectric layer 302, a transfer substrate provided with grooves (depth: 20 nm; track pitch: 0.32 μm) was adhered thereon, and a uniform resin layer was formed by rotating the entire disk. Next, the UV-curing resin was cured by irradiating UV light on this resin layer, and then the transfer substrate was stripped off. Through this step, a 25 μm thick optical separation layer 17 provided with guide grooves for guiding the laser beam 11 was formed on the side of the first information layer 21.

After this, a $TiO_2$ layer (thickness: 20 nm) serving as the transmittance adjusting layer 209, an Ag—Pd—Cu layer (thickness: 10 nm) serving as the reflective layer 208, a second interface layer 205 (thickness: 10 nm), a $Ge_{28}Sn_3Bi_2Te_{34}$ layer (thickness: 6 nm) serving as the recording layer 204, a first interface layer 203 (thickness: 5 nm), and a $(ZnS)_{80}(SiO_2)_{20}$ layer (thickness: 40 nm) serving as the first dielectric layer 202 were formed in this order by sputtering on the optical separation layer 17.

Lastly, a UV-curing resin was applied to the first dielectric layer 202, a polycarbonate sheet (diameter: 120 mm; thickness: 65 μm) was adhered to the first dielectric layer 202, and a uniform resin layer was formed by rotating the entire disk. After this, a transparent layer 13 of 75 μm thickness was formed by curing the resin through irradiation of UV light. Thereafter, an initialization step of crystallizing the recording layer 304 and the recording layer 204 with a laser beam was performed. In this manner, a plurality of samples with different materials for the first interface layer 203 and the second interface layer 205 were manufactured.

The recording sensitivity, signal strength and number of times of repeated rewriting of the first information layer 21 of the information recording media 20 of the resulting samples were evaluated using the recording/reproducing apparatus 32 shown in FIG. 7. For this, the wavelength of the laser beam 11 was set to 405 nm, the numerical aperture of the objective lens 34 was set to 0.85, the linear speed of the samples during measurement was set to 4.9 m/s and 9.8 m/s, and the shortest mark length (2 T) was set to 0.149 μm. The information was recorded in grooves. The method for measuring the recording sensitivity, the signal strength and the number of times of repeated rewriting is the same as in Working Example 1.

Tables 7 and 8 list the materials for the first interface layer 203 and the second interface layer 205 of the first information layer 21 of the information recording media 20 and the evaluation results regarding the recording sensitivity, signal strength and the repeated rewriting properties of the first information layer 21. Table 7 shows the results for a linear speed of 4.9 m/s (1×) and Table 8 shows the results for a linear speed of 9.8 m/s (2×). In the tables, Zr—Ga—O means $(ZrO_2)_{50}(Ga_2O_3)_{50}$ and Zr—Cr—O means $(ZrO_2)_{50}(Cr_2O_3)_{50}$. In this table, Zr—Cr—O/Zr—Ga—O means that the interface layer is formed using a $(ZrO_2)_{50}(Cr_2O_3)_{50}$ layer and a $(ZrO_2)_{50}(Ga_2O_3)_{50}$ layer, and that the $(ZrO_2)_{50}(Cr_2O_3)_{50}$ layer is arranged on the side on which the recording layer is formed. For the recording sensitivity at 1× speed, a value of less than 10.4 mW was taken to be "good", a value of at least 10.4 mW and less than 12 mW was taken to be "fair" and a value of 12 mW or more was taken to be "poor." For the recording sensitivity at 2× speed, a value of less than 12 mW was taken to be "good", a value of at least 12 mW and less than 14 mW was taken to be "fair" and a value of 14 mW or more was taken to be "poor." For the signal strength at both 1× speed and 2× speed, a value of at least 43 dB was taken to be "good", a value of at least 40 dB and less than 43 dB was taken to be "fair" and a value of less than 40 dB was taken to be "poor." As for the repeated rewriting properties, at both 1× speed and 2× speed, a number of times of repeated rewriting of at least 1000 was taken to be "good", a number of at least 500 and less than 1000 was taken to be "fair" and a number of less than 500 was taken to be "poor."

TABLE 7

| | | | linear speed: 4.9 m/s | | |
|---|---|---|---|---|---|
| sample No. | material of first interface layer 203 | material of second interface layer 205 | recording sensitivity | signal intensity | repeated rewriting properties |
| 5-1 | Ge—N | Ge—N | poor | poor | poor |
| 5-2 | Zr—Cr—O | Zr—Cr—O/ Zr—Ga—O | fair | good | good |
| 5-3 | Zr—Ga—O | Zr—Ga—O | good | good | good |
| 5-4 | Zr—Ga—O | Zr—Cr—O | fair | good | good |
| 5-5 | Zr—Cr—O | Zr—Ga—O | good | good | good |

TABLE 8 linear speed: 9.8 m/s

| sample No. | material of first interface layer 203 | material of second interface layer 205 | recording sensitivity | signal intensity | repeated rewriting properties |
|---|---|---|---|---|---|
| 5-1 | Ge—N | Ge—N | poor | poor | poor |
| 5-2 | Zr—Cr—O | Zr—Cr—O/Zr—Ga—O | fair | good | good |
| 5-3 | Zr—Ga—O | Zr—Ga—O | good | fair | fair |
| 5-4 | Zr—Ga—O | Zr—Cr—O | fair | fair | good |
| 5-5 | Zr—Cr—O | Zr—Ga—O | good | good | good |

As a result, it was found that in the sample 5-1 using Ge—N for the first interface layer 203 and the second interface layer 205 (comparative example), the recording sensitivity at 1× speed and 2× speed as well as the repeated rewriting properties at 1× speed are insufficient. Moreover, it was found that in the samples 3-2, 3-3, 3-4 and 3-5 using the above-noted compositions (I) to (IV) for the first interface layer 203 and the second interface layer 205, the recording sensitivity, the signal strength and the repeated rewriting properties are good. It was found that in particular in the sample 5-5, in which $(ZrO_2)_{50}(Cr_2O_3)_{50}$ is used for the first interface layer 203 and $(ZrO_2)_{50}(Ga_2O_3)_{50}$ is used for the second interface layer 205, the recording sensitivity, the signal strength and the repeated rewriting properties are all particularly good.

Additional Examples

Working Example 6

In Working Example 6, information recording media 20 as shown in FIG. 3 were fabricated, and the relation between the material of the second interface layer 205 of the first information layer 21 to the repeated rewriting properties of the first information layer 21 was examined. More specifically, samples of information recording media 20 including first information layers 21 with different materials for the second interface layer 205 were fabricated, and the number of times of repeated rewriting of the first information layer 21 were measured for each of these samples. It should be noted that the samples of this working example were fabricated in the same manner as the samples of Working Example 5, except that $(ZrO_2)_{50}(Ga_2O_3)_{50}$ was used for the first interface layer 203 and the materials listed in Table 3 used in Working Example 2 were used for the second interface layer 205.

As the result of evaluating the repeated rewriting properties in the same manner as in Working Example 2, it could be confirmed that when a material represented by the composition formula $(Ga_2O_3)_{C1}(Z1)_{100-C1}$ is used for the second interface layer 205, then the repeated rewriting properties are particularly good in the samples in which C1 is in the range of $10 \leq C1 \leq 90$, which is similar to the result obtained in Working Example 2.

Working Example 7

In Working Example 7, information recording media 23 as shown in FIG. 4 were manufactured, and the same measurements and evaluation as in Working Example 1 were performed.

The samples in this working example were manufactured as follows. First, a polycarbonate substrate (diameter: 120 mm; thickness: 0.6 mm) provided with guide grooves (depth: 40 nm; track pitch: 0.344 μm) for guiding the laser beam 11 was prepared as the substrate 24. Then, a $(ZnS)_{80}(SiO_2)_{20}$ layer (thickness: 60 nm) serving as the first dielectric layer 102, a first interface layer 103 (thickness: 5 nm), a $Ge_{28}Sn_3Bi_2Te_{34}$ layer (thickness: 10 nm) serving as the recording layer 104, a second interface layer 105 (thickness: 5 nm), a $(Bi_2O_3)_{50}(SiO_2)_{20}$ layer (thickness: 12 nm) serving as the second dielectric layer 106, and an Ag—Pd—Cu layer (thickness: 80 nm) serving as the reflective layer 108 were formed in this order by sputtering on this polycarbonate substrate.

After this, a UV-curing resin was applied on a separately prepared dummy substrate 27, and a uniform resin layer (thickness: 20 μm) was formed by adhering the reflective layer 108 of the information layer 25 formed on the substrate 24 to the dummy substrate 27 and rotating the entire disk. Then, the UV-curing resin was cured by irradiating UV light on this resin layer, thus adhering the information layer 25 to the dummy substrate 27 via the adhesive layer 26. Lastly, an initialization step of crystallizing the entire recording layer 104 with a laser beam was performed. As in the case of Working Example 1, the materials listed in Table 1 and Table 2 were used for the first interface layer 103 and the second interface layer 105, and five samples were fabricated.

The recording sensitivity, signal strength and number of times of repeated rewriting of the information layer 25 of the information recording media 23 of the resulting samples were measured using the same method as in Working Example 1 except the numerical aperture of the objective lens 34, the linear speed of the samples, and the shortest mark length. For this, the wavelength of the laser beam 11 was set to 405 nm, the numerical aperture of the objective lens 34 was set to 0.65, the linear speed of the samples during measurement was set to 8.6 m/s and 17.2 m/s, and the shortest mark length was set to 0.294 μm. The information was recorded in grooves.

As in Working Example 1, it was found that in particular in information layers 25 in which $(ZrO_2)_{50}(Cr_2O_3)_{50}$ or $(ZrO_2)_{50}(Ga_2O_3)_{50}$ is used for the first interface layer 103 and the second interface layer 105, the recording sensitivity, the signal strength and the repeated rewriting properties are good. It was found that in particular in the case that $(ZrO_2)_{50}(Cr_2O_3)_{50}$ is used for the first interface layer 103 and $(ZrO_2)_{50}(Ga_2O_3)_{50}$ is used for the second interface layer 105, an information recording medium 23 was obtained in which the recording sensitivity, the signal strength and the repeated rewriting properties of the information layer 25 are all particularly good.

Working Example 8

In Working Example 8, information recording media 31 as shown in FIG. 6 were fabricated, and the same measurements and evaluation as in Working Example 3 were performed.

The samples in this working example were manufactured as follows. First, a polycarbonate substrate (diameter: 120 mm; thickness: 0.6 mm) provided with guide grooves (depth: 40 nm; track pitch: 0.344 μm) for guiding the laser beam 11 was prepared as the substrate 24. Then, a $(ZnS)_{50}(SiO_2)_{20}$ layer (thickness: 40 nm) serving as the first dielectric layer 202, a $(ZrO_2)_{25}(SiO_2)_{25}(Cr_2O_3)_{50}$ layer (thickness: 5 nm) serving as the first interface layer 203, a $Ge_{28}Sn_3Bi_2Te_{34}$ layer (thickness: 6 nm) serving as the recording layer 204, a $(ZrO_2)_{25}(SiO_2)_{25}(Ga_2O_3)_{50}$ layer (thickness: 10 nm) serving as the second interface layer 205, an Ag—Pd—Cu layer (thickness: 10 nm) serving as the reflective layer 208, and a $TiO_2$ layer (thickness: 20 nm) serving as the transmittance adjusting layer 209 were formed in this order by sputtering on this polycarbonate substrate.

Moreover, a polycarbonate substrate (diameter: 120 mm; thickness: 0.58 mm) provided with guide grooves (depth: 40 nm; track pitch: 0.344 μm) for guiding the laser beam 11 was prepared as the substrate 30. Then, an Ag—Pd—Cu layer (thickness: 80 nm) serving as the reflective layer 208, a $(Bi_2O_3)_{80}(SiO_2)_{20}$ layer (thickness: 12 nm) serving as the second dielectric layer 306, a second interface layer 305 (thickness: 5 nm), a $Ge_{28}Sn_3Bi_2Te_{34}$ layer (thickness: 10 nm) serving as the recording layer 304, a first interface layer 303 (thickness: 5 nm), and a $(ZnS)_{80}(SiO_2)_{20}$ layer (thickness: 60 nm) serving as the first dielectric layer 302 were formed in this order by sputtering on this polycarbonate substrate.

After this, a UV-curing resin was applied on the first dielectric layer 302 of the second information layer 22 formed on this substrate 30, and a uniform resin layer (thickness: 20 μm) was formed by adhering this first dielectric layer 302 to the transmittance adjusting layer 209 of the first information layer 21 formed on the substrate 24, and rotating the entire disk. Next, the UV-curing resin was cured by irradiating UV light on this resin layer, thus forming an adhesive layer 26 through which the first information layer 21 and the second information layer 22 are glued together. After this, an initialization step of crystallizing the entire recording layer 304 of the second information layer 22 and the recording layer 204 of the first information layer 21 was performed by irradiation of a laser beam. As in the case of Working Example 3, the materials listed in Table 5 and Table 6 were used for the first interface layer 303 and the second interface layer 305, and five samples were fabricated.

The recording sensitivity, signal strength and number of times of repeated rewriting of the second information layer 22 of the information recording media 31 of the resulting samples were measured using the same method as in Working Example 3. For this, the wavelength of the laser beam 11 was set to 405 nm, the numerical aperture of the objective lens 34 was set to 0.65, the linear speed of the samples during measurement was set to 8.6 m/s and 17.2 m/s, and the shortest mark length was set to 0.294 μm. The information was recorded in grooves.

As in Working Example 3, it was found that in the second information layers 22 in which $(ZrO_2)_{50}(Cr_2O_3)_{50}$ or $(ZrO_2)_{50}(Ga_2O_3)_{50}$ is used for the first interface layer 303 and the second interface layer 305, the recording sensitivity, the signal strength and the repeated rewriting properties are good. It was found that in particular in the case that $(ZrO_2)_{50}(Cr_2O_3)_{50}$ is used for the first interface layer 303 and $(ZrO_2)_{50}(Ga_2O_3)_{50}$ is used for the second interface layer 305, an information recording medium 31 was obtained in which the recording sensitivity, the signal strength and the repeated rewriting properties of the second information layer 22 are all particularly good.

Working Example 9

In Working Example 9, information recording media 31 as shown in FIG. 6 were fabricated, and the same measurements and evaluation as in Working Example 5 were performed.

The samples in this working example were manufactured as follows. First, a polycarbonate substrate (diameter: 120 mm; thickness: 0.6 mm) provided with guide grooves (depth: 40 nm; track pitch: 0.344 μm) for guiding the laser beam 11 was prepared as the substrate 24. Then, a $(ZnS)_{50}(SiO_2)_{20}$ layer (thickness: 40 nm) serving as the first dielectric layer 202, a first interface layer 203 (thickness: 5 nm), a $Ge_{28}Sn_3Bi_2Te_{34}$ layer (thickness: 6 nm) serving as the recording layer 204, a second interface layer 205 (thickness: 10 nm), an Ag—Pd—Cu layer (thickness: 10 nm) serving as the reflective layer 208, and a $TiO_2$ layer (thickness: 20 nm) serving as the transmittance adjusting layer 209 were formed in this order by sputtering on this polycarbonate substrate.

Moreover, a polycarbonate substrate (diameter: 120 mm; thickness: 0.58 mm) provided with guide grooves (depth: 40 nm; track pitch: 0.344 μm) for guiding the laser beam 11 was prepared as the substrate 30. Then, an Ag—Pd—Cu layer (thickness: 80 nm) serving as the reflective layer 308, a $(Bi_2O_3)_{80}(SiO_2)_{20}$ layer (thickness: 12 nm) serving as the second dielectric layer 306, a $(ZrO_2)_{25}(SiO_2)_{25}(Ga_2O_3)_{50}$ layer (thickness: 5 nm) serving as the second interface layer 305, a $Ge_{28}Sn_3Bi_2Te_{34}$ layer (thickness: 10 nm) serving as the recording layer 304, a $(ZrO_2)_{25}(SiO_2)_{25}(Cr_2O_3)_{50}$ layer (thickness: 5 nm) serving as the first interface layer 303, a $(ZnS)_{80}(SiO_2)_{20}$ layer (thickness: 60 nm) serving as the first dielectric layer 302 were formed in this order by sputtering on this polycarbonate substrate.

After this, a UV-curing resin was applied on the first dielectric layer 302 of the second information layer 22 formed on this substrate 30, and a uniform resin layer (thickness: 20 μm) was formed by adhering this first dielectric layer 302 to the transmittance adjusting layer 209 of the first information layer 21 formed on the substrate 24, and rotating the entire disk. Next, the UV-curing resin was cured by irradiating UV light on this resin layer. Thus, an adhesive layer 26 through which the first information layer 21 and the second information layer 22 are glued together was formed. Lastly, an initialization step of crystallizing the entire recording layer 304 and the recording layer 204 by irradiation with a laser beam was performed. As in the case of Working Example 5, the materials listed in Table 7 and Table 8 were used for the first interface layer 203 and the second interface layer 205, and five samples were fabricated.

The recording sensitivity, signal strength and number of times of repeated rewriting of the first information layer 21 of the information recording media 31 of the resulting samples were measured using the same method as in Working Example 5. For this, the wavelength of the laser beam 11 was set to 405 nm, the numerical aperture of the objective lens 34 was set to 0.65, the linear speed of the samples during measurement was set to 8.6 m/s and 17.2 m/s, and the shortest mark length was set to 0.294 μm. The information was recorded in grooves.

As in Working Example 5, it was found that in the first information layer 21 in which $(ZrO_2)_{50}(Cr_2O_3)_{50}$ or $(ZrO_2)_{50}(Ga_2O_3)_{50}$ is used for the first interface layer 203 and the second interface layer 205, the recording sensitivity, the signal strength and the repeated rewriting properties are good. It was found that in particular in the case that $(ZrO_2)_{50}(Cr_2O_3)_{50}$ is used for the first interface layer 203 and $(ZrO_2)_{50}(Ga_2O_3)_{50}$ is used for the second interface layer 205, an information recording medium 31 was obtained in which the recording sensitivity, the signal strength and the repeated rewriting properties of the second information layer 23 are all particularly good.

Working Example 10

Also when in the samples fabricated in Working Example 1 to Working Example 9 a Cr-containing layer was provided between the recording layer and the Ga-containing layer provided as the interface layer, and the same measurements and evaluations were performed, the same results as in Working Example 1 to Working Example 9 were obtained. It should be noted that the composition of the Cr-containing layer that was provided between the recording layer and the Ga-containing layer was $(ZrO_2)_{50}(Cr_2O_3)_{50}$.

Working Example 11

Also when in the samples fabricated in Working Example 1 to Working Example 9, a C-containing layer containing C as its principal component was provided between the recording layer and the Ga-containing layer provided as the interface layer and/or between the Cr-containing layer and the recording layer, and the same measurements and evaluations were performed, the same results as in Working Example 1 to Working Example 9 were obtained. It should be noted that the C-containing layer used in this Example was a layer made of carbon.

Working Example 12

Also when the Ga-containing layer in Working Example 1 to Working Example 11 further included Si, or when a portion or all of the Zr in the Ga-containing layer was substituted with at least one element selected from Hf and Y, and the same measurements and evaluations were performed, the same results as in Working Example 1 to Working Example 11 were obtained. Also when the Ga-containing layer further comprised Cr, the same results as in Working Example 1 to Working Example 11 were obtained.

Working Example 13

Also when the Cr-containing layer in Working Example 1 to Working Example 12 further included Si, or when a portion or all of the Zr in the Cr-containing layer was substituted with at least one element selected from Hf and Y, and the same experiments were performed, the same results as in Working Example 1 to Working Example 12 were obtained.

Working Example 14

In Working Example 14, the electric information recording medium 38 shown in FIG. 8 was manufactured, and the phase change of the recording layers 412 and 422 by application of a current was confirmed.

As the substrate 39, an Si substrate was prepared, whose surface was subjected to a nitration process. On this surface, a Pt layer with a surface area of 6 µm×6 µm and a thickness of 0.1 µm serving as the lower electrode 40, a first information layer 41, a second information layer 42 and a Pt layer with a surface area of 5 µm×5 µm and a thickness of 0.1 µm serving as the upper electrode 43 were formed on in this order by sputtering.

The first information layer 41 was made by forming a $(ZrO_2)_{25}(SiO_2)_{25}(Cr_2O_3)_{50}$ layer with a surface area of 4.5 µm×5 µm and a thickness of 0.01 µm serving as the first interface layer 411, a $Ge_{22}Bi_2Te_{25}$ layer with a surface area of 5 µm×5 µm and a thickness of 0.1 µm serving as the recording layer 412, and a $(ZrO_2)_{25}(SiO_2)_{25}(Ga_2O_3)_{50}$ layer with a surface area of 4.5 µm×5 µm and a thickness of 0.01 µm serving as the second interface layer 413, by sputtering in this order on the lower electrode 40.

The second information layer 42 was made by forming a $(ZrO_2)_{25}(SiO_2)_{25}(Cr_2O_3)_{50}$ layer with a surface area of 4.5 µm×5 µm and a thickness of 0.01 µm serving as the second interface layer 421, a $Sb_{70}Te_{25}Ge_5$ layer with a surface area of 5 µm×5 µm and a thickness of 0.1 µm serving as the recording layer 422, and a $(ZrO_2)_{25}(SiO_2)_{25}(Ga_2O_3)_{50}$ layer with a surface area of 4.5 µm×5 µm and a thickness of 0.01 µm serving as the second interface layer 423, by sputtering in this order on the second interface layer 413 of the first information layer 41.

It should be noted that the first interface layers 411 and 421 and the second interface layers 413 and 423 formed as above are isolators. Consequently, in order to let a current flow through the recording layers 412 and 422, the first interface layers 411 and 421 and the second interface layers 413 and 423 are formed with a surface area that is smaller than that of the recording layers 412 and 422, and contacting portions are provided, so that the lower electrode 40, the recording layer 412 of the first information layer 41, the recording layer 422 of the second information layer 422 and the upper electrode 43 are electrically connected to one another.

After this, the lower electrode 40 and the upper electrode 43 were bonded with Au lead wires, and the electric information recording/reproducing apparatus 44 was connected to the electric information recording medium 38 via the application portions 45. With this electric information recording/reproducing apparatus 44, the pulse power source 48 was connected via the switch 47 between the lower electrode 40 and the upper electrode 43, and the change of the resistance due to phase changes of the recording layers 412 and 422 was detected with the resistance measuring device 46 connected via the switch 49 between the lower electrode 40 and the upper electrode 43.

In this embodiment, the melting point $T_{m1}$ of the recording layer 412 of the first information layer 41 was 630° C., its crystallization temperature $T_{x1}$ was 170° C., and its crystallization time $t_{x1}$ was 100 ns. Moreover, the recording layer 412 had an amorphous phase resistance $r_{a1}$ of 500Ω, and a crystalline resistance $r_{c1}$ of 10 Ω.

Also, the melting point $T_{m2}$ of the recording layer 422 of the second information layer 42 was 550° C., its crystallization temperature $T_{x2}$ was 200° C., and its crystallization time $t_{x2}$ was 50 ns. Furthermore, the recording layer 422 had an amorphous phase resistance $r_{a2}$ of 800Ω, and a crystalline resistance $r_{c2}$ of 20 Ω.

FIG. 11 shows an example of recording and erasing pulse waveforms that are output from the pulse power source 48 of the electric information recording/reproducing apparatus 44. In FIG. 11, $I_{c1}$, $I_{c2}$, $I_{a1}$, $I_{a2}$, $t_{c1}$, $t_{c2}$, $t_{a1}$, and $t_{a2}$ represent the following:

$I_{c1}$, $t_{c1}$: current and time necessary for letting the recording layer 412 of the first information layer 41 make a transition from amorphous to crystalline;

$I_{c2}$, $t_{c2}$: current and time necessary for letting the recording layer 422 of the second information layer 42 make a transition from amorphous to crystalline;

$I_{a1}$, $t_{a1}$: current and time necessary for letting the recording layer 412 of the first information layer 41 make a transition from crystalline to amorphous;

$I_{a2}$, $t_{a2}$: current and time necessary for letting the recording layer 422 of the second information layer 42 make a transition from crystalline to amorphous;

The relation of the current pulses to the recording layer 412 of the first information layer 41 (referred to below for convenience's sake as "first recording layer 412") and the recording layer 422 of the second information layer 42 (referred to below for convenience's sake as "second recording layer 422) is explained below.

When the first recording layer 412 and the second recording layer 422 are both in the amorphous phase (this referred to as "state 1" below), and a current pulse of $I_{c1}$=5 mA, $t_{c1}$=150 ns was applied with the recording waveform 501 in FIG. 11 between the lower electrode 40 and the upper electrode 43, then only the first recording layer 412 made a transition from the amorphous phase to the crystalline phase (this is referred to as "state 2" below). When in state 1 a current pulse of $I_{c2}$=10 mA, $t_{c2}$=100 ns was applied with the recording waveform 502 in FIG. 11 between the lower electrode 40 and the upper electrode 43, then only the second recording layer 422 made a transition from the amorphous phase to the crystalline phase (this is referred to as "state 3" below). When in state 1 a current pulse of $I_{c2}$=10 mA, $t_{c1}$=150 ns was applied with the recording waveform 502 in FIG. 11 between the lower electrode 40 and the upper electrode 43, then both the first recording layer 412 and the second recording layer 422 made a transition from the amorphous phase to the crystalline phase (this is referred to as "state 4" below).

Next, when in state 4, in which both the first recording layer 412 and the second recording layer 422 are in the crystalline phase, a current pulse of $I_{a1}$=20 mA, $I_{c2}$=10 mA, $t_{c2}$=100 ns was applied with the recording waveform 504 in FIG. 11 between the lower electrode 40 and the upper electrode 43, then only the first recording layer 412 made a transition from the crystalline phase to the amorphous phase (state 3). When in state 4 a current pulse of $I_{a2}$=15 mA, $t_{a2}$=50 ns was applied with the recording waveform 505 in FIG. 11 between the lower electrode 40 and the upper electrode 43, then only the second recording layer 422 made a transition from the crystalline phase to the amorphous phase (state 2). And when in state 4 a current pulse of $I_{a1}$=20 mA, $t_{a1}$=50 ns was applied with the erasing waveform 506 in FIG. 11 between the lower electrode 40 and the upper electrode 43, then both the first recording layer 412 and the second recording layer 422 made a transition from the crystalline phase to the amorphous phase (state 1).

When in state 2 or state 3 a current pulse of $I_{c2}$=10 mA, $t_{c1}$=150 ns was applied with the recording waveform 503 in FIG. 11, then both the first recording layer 412 and the second recording layer 422 made a transition from the amorphous phase to the crystalline phase (state 4). Also, when in state 2 or state 3 a current pulse of $I_{a1}$=20 mA, $I_{c2}$=10 mA, $t_{c1}$=150 ns, $t_{a1}$=50 ns was applied with the erasing waveform 507 in FIG. 11, then both the first recording layer 412 and the second recording layer 422 made a transition from the crystalline phase to the amorphous phase (state 1). When in state 2 a current pulse of $I_{a1}$=20 mA, $I_{c2}$=10 mA, $t_{c2}$=100 ns, $t_{a1}$=50 ns was applied with the recording waveform 508 in FIG. 11, then the first recording layer 412 made a transition from the crystalline phase to the amorphous phase and the second recording layer 422 made a transition from the amorphous phase to the crystalline phase (state 3). Also, when in state 3 a current pulse of $I_{a2}$=15 mA, $I_{c1}$=5 mA, $t_{c1}$=150 ns, $t_{a2}$=50 ns was applied with the recording waveform 509 in FIG. 11, then the first recording layer 412 made a transition from the amorphous phase to the crystalline phase and the second recording layer 422 made a transition from the crystalline phase to the amorphous phase (state 2).

The foregoing results showed that with the electric phase-changing information recording medium 38 of FIG. 8, the phases of the first recording layer 412 and the second recording layer 422 could be changed electrically between the crystalline phase and the amorphous phase, and four states (state 1: first recording layer 412 and second recording layer 422 both amorphous; state 2: first recording layer 412 crystalline and second recording layer 422 amorphous; state 3: first recording layer 412 amorphous and second recording layer 422 crystalline; state 4: first recording layer 412 and second recording layer 422 both crystalline) could be realized.

Moreover, when the number of times of repeated rewriting of the electric phase-changing information recording medium 38 was measured, it was confirmed that this number was at least ten times higher than in the case where the information layers 41 and 42 were not provided with the first interface layer 411, 421 and second interface layers 413, 423. This is because the first interface layer 411, 421 and second interface layers 413, 423 suppressed the migration of substances from the lower electrode 40 and the upper electrode 43 into the first recording layer 412 and the second recording layer 422.

Thus, the information recording medium of the present invention has the quality that recorded information can be retained for a long time (non-volatility) and is suitable for high-density rewritable or write-once optical disks, for example. It can further be applied to electric non-volatile memories.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. An information recording medium comprising:
   a substrate; and
   an information layer provided on the substrate, the information layer comprising:
   a recording layer whose phase can be changed between a crystalline phase and an amorphous phase by irradiation with a laser beam or application of electric energy;
   a Cr-containing layer comprising at least Cr and O, arranged in contact with a first surface of the recording layer;
   a Ga-containing layer comprising at least Ga and O, arranged in contact with a second surface of the recording layer, and
   wherein the Cr-containing layer, the recording layer, and the Ga-containing layer are arranged in this order from a side from which the laser beam is incident, and
   the Ga-containing layer comprises a material that can be expressed by the following composition formula:

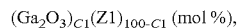
   $(Ga_2O_3)_{C1}(Z1)_{100-C1}$ (mol %), where Z1 is at least one oxide selected from $ZrO_2$, $HfO_2$, $Y_2O_3$ and $SiO_2$, and C1 satisfies:

$50 \leq C1 \leq 90$.

2. The information recording medium according to claim 1, wherein the information layer further comprises at least one of a first dielectric layer arranged closer to the side from which the laser beam is incident than the Cr-containing layer, and a second dielectric layer arranged further away from the side from which the laser beam is incident than the Ga-containing layer.

3. The information recording medium according to claim 1, wherein the information layer further comprises a reflective layer arranged further away from the side from which the laser beam is incident than the Ga-containing layer.

4. The information recording medium according to claim 1, wherein the information recording medium is a multi-layer information recording medium comprising first to N-th information layers (where N is an integer of 2 or larger), and wherein at least one of the first to N-th information layers is said information layer.

5. The information recording medium according to claim 4,
   wherein the recording layer's phase can be changed between a crystalline phase and an amorphous phase by irradiation with a laser beam;

wherein the first to N-th information layers are arranged in that order from the side from which the laser beam is incident;

wherein at least the first information layer is said information layer, and the first information layer comprises a first dielectric layer, the Cr-containing layer, the recording layer, the Ga-containing layer, a reflective layer and a transmittance adjusting layer arranged in that order from the side from which the laser beam is incident.

6. The information recording medium according to claim 1, wherein the Cr-containing layer further comprises at least one element selected from Zr, Hf, Y and Si.

7. The information recording medium according to claim 6, wherein the Cr-containing layer comprises $Cr_2O_3$ and at least one oxide selected from $ZrO_2$, $HfO_2$, $Y_2O_3$ and $SiO_2$.

8. An information recording medium comprising:
a substrate; and
an information layer provided on the substrate, the information layer comprising:
a recording layer whose phase can be changed between a crystalline phase and an amorphous phase by irradiation with a laser beam or application of electric energy;
a Cr-containing layer comprising at least Cr and O, arranged on a side of a first surface of the recording layer;
a Ga-containing layer comprising at least Ga and O, arranged on a side of a second surface of the recording layer,
a C-containing layer containing C as its principal component and arranged in contact with the recording layer between the recording layer and the Cr-containing layer and/or between the recording layer and the Ga-containing layer; and
wherein the Cr-containing layer is arranged closer to a side from which the laser beam is incident than the recording layer, and the Ga-containing layer is arranged further away from the side from which the laser beam is incident than the recording layer, and
the Ga-containing layer comprises a material that can be expressed by the following composition formula:

$(Ga_2O_3)_{C1}(Z1)_{100-C1}$ (mol %), where Z1 is at least one oxide selected from $ZrO_2$, $HfO_2$, $Y_2O_3$ and $SiO_2$, and C1 satisfies:

$50 \leq C \leq 90$.

9. The information recording medium according to claim 8, wherein the information layer further comprises at least one of a first dielectric layer arranged closer to the side from which the laser beam is incident than the Cr-containing layer, and a second dielectric layer arranged further away from the side from which the laser beam is incident than the Ga-containing layer.

10. The information recording medium according to claim 8, wherein the information layer further comprises a reflective layer arranged further away from the side from which the laser beam is incident than the Gs-containing layer.

11. The information recording medium according to claim 8, wherein the information recording medium is a multi-layer information recording medium comprising first to N-th information layers (where N is an integer of 2 or larger), and wherein at least one of the first to N-th information layers is said information layer.

12. The information recording medium according to claim 11,
wherein the recording layer's phase can be changed between a crystalline phase and an amorphous phase by irradiation with a laser beam;
wherein the first to N-th information layers are arranged in that order from the side from which the laser beam is incident;
wherein at least the first information layer is said information layer, and the first information layer further comprises a first dielectric layer arranged closer to the side from which the laser beam is incident than the Cr-containing layer, and a reflective layer and a transmittance adjusting layer arranged in that order further away from the side from which the laser beam is incident than the Ga-containing layer.

13. The information recording medium according to claim 8, wherein the Cr-containing layer further comprises at least one element selected from Zr, Hf, Y and Si.

14. The information recording medium according to claim 13, wherein the Cr-containing layer comprises $Cr_2O_3$ and at least one oxide selected from $ZrO_2$, $HfO_2$, $Y_2O_3$ and $SiO_2$.

15. A method for manufacturing an information recording medium comprising:
a substrate;
an information layer provided on the substrate, the information layer comprising:
a recording layer;
a Cr-containing layer; and
a Ga-containing layer,
the method comprising:
(a) a step of forming a Cr-containing layer using a Cr-containing sputtering target comprising at least Cr and O while arranging the Cr-containing layer in contact with a first surface of the recording layer;
(b) a step of forming a recording layer whose phase can be changed between a crystalline phase and an amorphous phase by irradiation with a laser beam or application of electric energy;
(c) a step of forming a Ga-containing layer using a Ga-containing sputtering target comprising at least Ga and O or $Ga_2O_3$ and at least one oxide selected from $ZrO_2$, $HfO_2$, $Y_2O_3$ and $SiO_2$ while arranging the Ga-containing layer in contact with a second surface of the recording layer, wherein the Ga-containing layer comprises a material that can be expressed by the following composition formula:

$(Ga_2O_3)_{C1}(Z1)_{100-C1}$ (mol %)

where Z1 is the at least one oxide selected from $ZrO_2$, $HfO_2$, $Y_2O_3$ and $SiO_2$, and C1 satisfies:

$50 \leq C1 \leq 90$;

wherein the steps (a) to (c) are carried out in the order of step (a), step (b), step (c) or in the order of step (c), step (b), step (a), and the Cr-containing layer, the recording layer, and the Ga-containing layer are arranged in this order from a side from which the laser beam is incident.

16. The information recording medium manufacturing method according to claim 15, wherein the Cr-containing sputtering target further comprises at least one element selected from Zr, Hf, Y and Si.

17. The information recording medium manufacturing method according to claim 16, wherein the Cr-containing sputtering target comprises $Cr_2O_3$ and at least one oxide selected from $ZrO_2$, $HfO_2$, $Y_2O_3$ and $SiO_2$.

18. A method for manufacturing an information recording medium comprising:

a substrate;
an information layer provided on the substrate, the information layer comprising:
a recording layer;
a Cr-containing layer;
a Ga-containing layer; and
a C-containing layer,
the method comprising:
(a) a step of forming a Cr-containing layer using a Cr-containing sputtering target comprising at least Cr and O while arranging the Cr-containing layer in contact with a first surface of the recording layer;
(b) a step of forming a recording layer whose phase can be changed between a crystalline phase and an amorphous phase by irradiation with a laser beam or application of electric energy;
(c) a step of forming a Ga-containing layer using a Ga-containing sputtering target comprising at least Ga and O or $Ga_2O_3$ and at least one oxide selected from $ZrO_2$, $HfO_2$, $Y_2O_3$ and $SiO_2$ while arranging the Ga-containing layer in contact with a second surface of the recording layer, wherein the Ga-containing layer comprises a material that can be expressed by the following composition formula:

$(Ga_2O_3)_{C1}(Z1)_{100-C1}$ (mol %)

where Z1 is the at least one oxide selected from $ZrO_2$, $HfO_2$, $Y_2O_3$ and $SiO_2$, and C1 satisfies:

$50 \leq C1 \leq 90$;

wherein the steps (a) to (c) are carried out in the order of step (a), step (b), step (c) or in the order of step (c), step (b), step (a); and
further comprising (d) a step of forming a C-containing layer using a C-containing sputtering target comprising C as its principal component while arranging the C-containing layer, in contact with the recording layer, between the recording layer and the Cr-containing layer and/or between recording layer and the Ga-containing layer,
wherein the step (d) is carried out between step (a) and step (b) and/or between step (b) and step (c).

19. The information recording medium manufacturing method according to claim 18, wherein the Cr-containing sputtering target further comprises at least one element selected from Zr, Hf, Y and Si.

20. The information recording medium manufacturing method according to claim 18, wherein the Cr-containing sputtering target comprises $Cr_2O_3$ and at least one oxide selected from $ZrO_2$, $HfO_2$, $Y_2O_3$ and $SiO_2$.

21. The information recording medium according to claim 1, wherein the Ga-containing layer comprises a material that can be expressed by the following composition formula:

$(Ga_2O_3)_{50}(Z1)_{50}$ (mol %)

where Z1 is at least one oxide selected from $ZrO_2$, $HfO_2$, $Y_2O_3$ and $SiO_2$.

22. The information recording medium according to claim 8, wherein the Ga-containing layer comprises a material that can be expressed by the following composition formula:

$(Ga_2O_3)_{50}(Z1)_{50}$ (mol %)

where Z1 is at least one oxide selected from $ZrO_2$, $HfO_2$, $Y_2O_3$ and $SiO_2$.

23. The method for manufacturing an information recording medium according to claim 15, wherein the Ga-containing layer comprises a material that can be expressed by the following composition formula:

$(Ga_2O_3)_{50}(Z1)_{50}$ (mol %)

where Z1 is at least one oxide selected from $ZrO_2$, $HfO_2$, $Y_2O_3$ and $SiO_2$.

24. The method for manufacturing an information recording medium according to claim 18, wherein the Ga-containing layer comprises a material that can be expressed by the following composition formula:

$(Ga_2O_3)_{50}(Z1)_{50}$ (mol %)

where Z1 is at least one oxide selected from $ZrO_2$, $HfO_2$, $Y_2O_3$ and $SiO_2$.

* * * * *

UNITED STATES PATENT AND TRADEMARK OFFICE
CERTIFICATE OF CORRECTION

PATENT NO. : 7,858,290 B2
APPLICATION NO. : 10/953687
DATED : December 28, 2010
INVENTOR(S) : Nishihara et al.

It is certified that error appears in the above-identified patent and that said Letters Patent is hereby corrected as shown below:

Column 51, line 47: "$50 \leq C \leq 90$" should be --$50 \leq C1 \leq 90$--.

Signed and Sealed this
Twenty-fourth Day of May, 2011

David J. Kappos
*Director of the United States Patent and Trademark Office*